(12) United States Patent
Molakandov et al.

(10) Patent No.: US 11,679,133 B2
(45) Date of Patent: Jun. 20, 2023

(54) METHODS FOR DIFFERENTIATING AND PURIFYING PANCREATIC ENDOCRINE CELLS

(71) Applicants: Kadimastem Ltd., Nes Ziona (IL); Yeda Research and Development Co. Ltd., Rehovot (IL)

(72) Inventors: Kfir Molakandov, Yahud (IL); Neta Lavon, Nes-Ziona (IL); Avital Beck, Rehovot (IL); Michel Revel, Rehovot (IL); Ofer Elhanani, Tel-Aviv (IL); Yoav Soen, Rehovot (IL); Michael Walker, Rehovot (IL); Arik Hasson, Kiryat-Ono (IL)

(73) Assignees: Kadimastem Ltd., Nes Ziona (IL); Yeda Research and Development Co. Ltd., Rehovot (IL)

( * ) Notice: Subject to any disclaimer, the term of this patent is extended or adjusted under 35 U.S.C. 154(b) by 602 days.

(21) Appl. No.: 15/780,153

(22) PCT Filed: Nov. 28, 2016

(86) PCT No.: PCT/IL2016/051274
§ 371 (c)(1),
(2) Date: May 30, 2018

(87) PCT Pub. No.: WO2017/094001
PCT Pub. Date: Jun. 8, 2017

(65) Prior Publication Data
US 2018/0369290 A1    Dec. 27, 2018

Related U.S. Application Data

(60) Provisional application No. 62/366,651, filed on Jul. 26, 2016, provisional application No. 62/260,669, filed on Nov. 30, 2015.

(51) Int. Cl.
| | |
|---|---|
| *A61K 35/39* | (2015.01) |
| *C12N 5/00* | (2006.01) |
| *C12N 5/071* | (2010.01) |
| *A61P 5/50* | (2006.01) |
| *A61P 3/10* | (2006.01) |

(52) U.S. Cl.
CPC ............... *A61K 35/39* (2013.01); *A61P 3/10* (2018.01); *A61P 5/50* (2018.01); *C12N 5/0676* (2013.01); *C12N 2500/25* (2013.01); *C12N 2500/34* (2013.01); *C12N 2500/38* (2013.01); *C12N 2501/599* (2013.01); *C12N 2506/02* (2013.01); *C12N 2506/45* (2013.01)

(58) Field of Classification Search
CPC . A61K 35/39; C12N 5/0676; C12N 2501/599
See application file for complete search history.

(56) References Cited

U.S. PATENT DOCUMENTS

2013/0122520 A1*  5/2013  Kelly et al. .......... C12N 5/0676
                                                          435/7.21

FOREIGN PATENT DOCUMENTS

| AU | 2015200985 | 3/2015 | |
|---|---|---|---|
| JP | 2007-503815 | 3/2007 | |
| WO | WO 2005/021728 | 3/2005 | |
| WO | WO 2007/025306 | 7/2007 | |
| WO | WO 2008/026198 | 3/2008 | |
| WO | WO 2009/131568 | 10/2009 | |
| WO | WO 2010/042669 | 4/2010 | |
| WO | WO 2013/076726 | 5/2013 | |
| WO | 2014/030166 A1 | 2/2014 | |
| WO | WO 2014/030166 A1 * | 2/2014 | ............ C12N 5/071 |
| WO | 2014/165663 A1 | 10/2014 | |

OTHER PUBLICATIONS

BD Biosciences "Purified Mouse Anti-Human HLA-ABC: Clone G46-2.6 (RUO)", Webpage, 6 pages, accessed Dec. 1, 2020. (Year: 2020).*
International Preliminary Report on Patentability dated Dec. 14, 2017 From the International Preliminary Examining Authority Re. Application No. PCT/IL2016/05127. (16 Pages).
Office Action dated Sep. 15, 2019 From the Israel Patent Office Re. Application No. 259702. (2 Pages).
Office Action dated Jun. 18, 2018 From the Israel Patent Office Re. Application No. 259702. (1 Page).
Supplementary European Search Report and the European Search Opinion dated Jul. 19, 2019 From the European Patent Office Re. Application No. 16870121.7. (9 Pages).
Supplementary Partial European Search Report and the Provisional Opinion Dated Apr. 17, 2019 From the European Patent Office Re. Application No. 16870121.7. (11 Pages(.
Boucherie et al. "Chimerization of Astroglial Population in the Lumbar Spinal Cord After Mesenchymal Stem Cell Transplantation Prolongs Survival in A Rat Model of Amyotrophic Lateral Sclerosis", Journal of Neuroscience, 87(9): 2034-2046, Pubhshed Online Mar. 6, 2009.
Gupta et al. "Human Embryonic Stem Cell Derived Astrocytes Mediate Non-Cell-Autonomous Neuroprotection Through Endogenous and Drug-Induced Mechanisms", Cell Death and Differentiation, 19(5): 779-787, Published Online Nov. 18, 2011.
Lepore et al. "Focal Transplantation-Based Astrocyte Replacement Is Neuroprotective in A Model of Motor Neuron Disease", Nature Neuroscience, 11(11): 1294-1301, Published Online Oct. 19, 2008.
Roybon et al. "Human Stem Cell-Derived Spinal Cord Astrocytes With Defined Mature or Reactive Phenotypes", Cell Reports, 4(5): 1035-1048, Sep. 12, 2013.
Serio et al. Astrocyte Pathology and the Absence of Non-Cell Autonomy in an Induced Pluripotent Stem Cell Model of TDP-43 Proteinopathy, Proceedings of the National Academy of Sciences, 110(12):4697-4702,Mar. 19, 2013.

(Continued)

*Primary Examiner* — James D Schultz
*Assistant Examiner* — James Joseph Graber

(57) ABSTRACT

The present invention relates to compositions and methods comprising cell surface markers for pluripotent-derived cells, in particular, pancreatic endoderm-type cells, derived from pluripotent stem cells.

6 Claims, 14 Drawing Sheets

(56) References Cited

OTHER PUBLICATIONS

Sugiyama et al. "Conserved Markers of Fetal Pancreatic Epithelium Permit Prospective Isolation of Islet Progenitor Cells by FACS", Proc. Natl. Acad. Sci. USA, PNAS, XP0023476716, 104(1): 175-180, Jan. 2, 2007.
Suzuki et al. "GDNF Secreting Human Neural Progenitor Cells Protect Dying Motor Neurons, But Not Their Projection to Muscle, in A Rat Model of Familial ALS", PLoS ONE, 2(8): e689-1-e689-14, Aug. 1, 2007.
Woehrling et al. "Development of a Neurotoxicity Test-System, Using Human Post-Mitotic, Astrocytic and Neuronal Cell Lines In Co-Culture", Toxicology in Vitro, 21(7): 1241-1246, Oct. 2007.
International Search Report of PCT/IL2016/051274 dated Apr. 4, 2017.
Written Opinion of PCT/IL201/051274 dated Apr. 4, 2017.
Notification of Reasons for Rejection dated Sep. 8, 2020 From the Japan Patent Office Re. Application No. 2018-546931 and Its Translation Into English. (10 Pages).
Relatorio de Busca e Parecer [Search Report and Opinion] dated Mar. 18, 2021 From the Servico Publico Federal, Ministerio da Economia, Instituto Macional da Propriedade Industrial do Brasil Re. Application No. BR11201801094-6 and Its Translation Into English. (8 Pages).
Office Action dated Oct. 20, 2022 From the Israel Patent Office Re. Application No. 293289. (4 Pages).

* cited by examiner

METHODS FOR DIFFERENTIATING AND PURIFYING PANCREATIC ENDOCRINE CELLS

FIELD OF THE INVENTION

The present invention, in some embodiments thereof, relates to insulin-producing cells derived from pluripotent stem cells, and to methods of differentiating and purifying the same. The present invention further relates to compositions and methods comprising cell surface markers for human pluripotent-derived cells, in particular, pancreatic endocrine-type cells, derived from human pluripotent stem cells.

BACKGROUND OF THE INVENTION

In type I diabetes, the insulin producing cells, or beta (β)-cells in the islets of Langerhans, are destroyed. Islets of Langerhans are specialized cell aggregates constituting the endocrine pancreas, including β-cells producing insulin (about 55% of the endocrine pancreas in humans), α-cells producing glucagon (about 35% in humans), δ-cells producing somatostatin (3-10%), PP cells producing pancreatic polypeptides (3-5%), and ε-cells producing ghrelin (less than 1%). Insulin and glucagon are major regulators of blood glucose levels. In response to high glucose levels, insulin stimulates the uptake of glucose by peripheral tissues such as fat, liver and muscle cells in particular, where it is converted into energy or stored into fat and glycogen, and therefore lowers the blood glucose levels. Glucagon, conversely, stimulates the release of glucose from fat and from glycogen stores in situations of hypoglycemia.

Type I diabetes patients are dependent on daily injections of insulin to decrease their blood glucose levels. However, over years, cumulative damage of hyperglycemia periods on the vasculature leads to severe deterioration of the patient's health. The physiological regulation of blood glucose as well as the general health of such patients can be dramatically improved by the transplantation of human islets from cadaveric donors. However, the need for such transplants is much larger than the availability of islet cells from cadaveric donors. In fact, only a few thousand transplantations can be done worldwide every year for a potential number of 130 million patients who could benefit from such a treatment. Therefore additional sources of pancreatic islet cells are needed.

A variety of techniques have been previously employed in an attempt to isolate pancreatic beta cells. U.S. Pat. No. 9,045,736 teaches a method of enriching for cells expressing chromogranin A. U.S. Patent Application 20150157668 to some of the inventors of the present invention, teaches a method of isolating an enriched population of at least one distinct type of pancreatic cells from a heterogeneous population of cells.

Human pluripotent stem cells have the potential to produce differentiated cell types comprising all human somatic tissues and organs. Cell therapy treatments of insulin dependent diabetes will be facilitated by the production of unlimited numbers of pancreatic cells that can and will be able to function similarly to human islets. Accordingly, there is a high demand for producing pancreatic islet-like cells derived from pluripotent stem cells, as well as for reliable methods for differentiating and purifying such cells before transplantation.

SUMMARY OF THE INVENTION

The present invention provides methods of differentiation, isolation and purification of pancreatic endocrine-type cells using newly identified markers and selection means. More specifically, the present invention provides efficient isolation of pancreatic endocrine-type cells using specific cell surface markers.

The present invention further provides novel combinations of cell markers suitable for identifying or enriching pancreatic endocrine-type cells. Use of the markers and of the isolated cells in the treatment of diabetes is also provided.

Pancreatic beta cell specific surface markers are of particular interest as they may facilitate purification of mature, functional insulin-producing beta cells suitable for transplantation.

According to one aspect of the present invention, a method for enriching pancreatic endocrine cells is provided, the method comprises: a) exposing an in vitro cell population comprising pancreatic endocrine cells to a ligand that binds a cell-surface marker selected from the group consisting of CD49A, CD29, CD99, CD10, CD59, CD141, CD165, G46-2.6, CD44, CD57, CD294, CD66c, CD340, CD26, CD49f and CD73; and b) selecting cells from said in vitro cell population that express a marker selected from the group consisting of CD49A, CD29, CD99, CD10, CD59, CD141, CD165, G46-2.6, CD44, CD57 and/or selecting cells from said in vitro cell population that do not express a marker selected from the group consisting of CD294, CD66c, CD340, CD26, CD49f and CD73, thereby enriching for pancreatic endocrine cells.

According to some embodiments, the pancreatic endocrine cells are enriched for using positive sorting or selection with the cell-surface marker CD49A or G46-2.6.

According to some embodiments, the cell surface marker CD49A or G46-2.6 is the first marker used for selection. According to some embodiments, further selection with at least one additional cell-surface marker is used.

According to some embodiments, the pancreatic endocrine cells are isolated from culture derived committed cell lineages isolated from cultures derived from embryonic pluripotent stem cells, adult stem cells, or induced pluripotent stem cells.

According to some embodiments of the present invention, the ligand is an antibody or binding fragment thereof. According to some embodiments, said antibody is a monoclonal antibody. According to other embodiments, said antibody is a polyclonal antibody.

According to some embodiments, the pancreatic endocrine cells express NKX6.1. According to some embodiments, the pancreatic endocrine cells express pancreatic and duodenal homeobox gene 1 (PDX1). According to some embodiments, the pancreatic endocrine cells express insulin. According to some embodiments, the pancreatic endocrine cells express MAFA.

According to some embodiments, said ligand is associated with a detectable label. According to some embodiments, said ligand is associated with a magnetic particle. According to some embodiments, said cells are separated by Fluorescence Activated Cell Sorting (FACS) or Magnetic Cell Sorting (MACS).

According to another aspect of the present invention, an enriched population of human pancreatic endocrine cells is provided, isolated according to the method described herein.

According to a further aspect of the present invention, there is provided a method of prevention or treatment of diabetes comprising transplantation of a population of human pancreatic endocrine cells of the present invention to a human subject in need thereof, wherein the population of human pancreatic endocrine cells comprises mature, functional insulin-producing beta cells.

According to some embodiments, the human pancreatic endocrine cells are isolated from culture derived from committed cell lineages isolated from cultures derived from embryonic pluripotent stem cells, adult stem cells, or induced pluripotent stem cells.

According to a further aspect of the present invention, there is provided a method of preparing NKX6-1+, PDX1+, C-peptide+, insulin producing beta cells from human pluripotent cells grown under xeno-free culture conditions comprising the steps of: (a) culturing pluripotent cells on a xeno-free substrate in a xeno-free growth medium; (b) differentiating in suspension the human pluripotent stem cells into NKX6-1+, PDX1+, C-peptide+, insulin producing beta cells, in the presence of at least three differentiation agents.

According to some embodiments, the xeno-free substrate is selected from the group consisting of vitronectin, Synthemax, Cellstart, StemAdhere, Collagen and laminin.

According to some embodiments, the xeno-free growth medium is selected from the group consisting of NutriStem™, and E8™ medium.

According to some embodiments, the human pluripotent cells are dissociated by EDTA.

According to some embodiments, the at least three differentiation agents are selected from the group consisting of Ascorbic acid, CHIR, Activin A, LDN-193189, keratinocyte growth factor (KGF), and sodium bicarbonate.

According to some embodiments, the Ascorbic acid is added during the all differentiation process.

According to some embodiments, the method further comprises exposing the insulin producing beta cells to a ligand that binds a cell-surface marker selected from the group consisting of CD49A, CD29, CD99, CD10, CD59, CD141, CD165, G46-2.6, CD44, CD57, CD294, CD66c, CD340, CD26, CD49f and CD73; and selecting cells from said cell population that express a marker selected from the group consisting of CD49A, CD29, CD99, CD10, CD59, CD141, CD165, G46-2.6, CD44, CD57 and/or selecting cells from said cell population that do not express a marker selected from the group consisting of CD294, CD66c, CD340, CD26, CD49f and CD73, thereby enriching for pancreatic endocrine cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
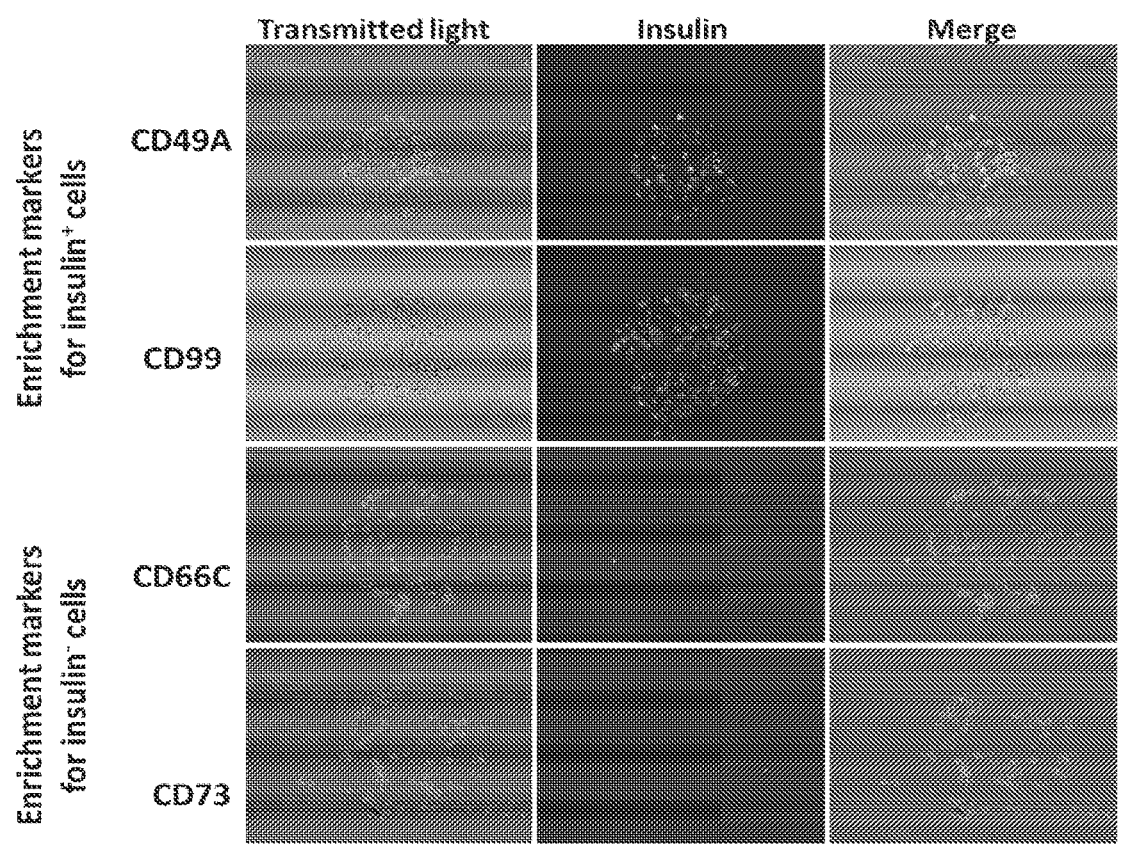
FIG. 1 demonstrates the functional cell-capture screening (FCCS). ES-derived pancreatic cells were analyzed by functional cell capture screening. Following a short incubation of single cells on the cell surface antibody array, cells were fixed and stained for insulin (green). Using high content screening analysis, the total number of bound cells to each spot was determined. In addition, the percentage of insulin+ cells in each spot was calculated. An example of output signal for 4 markers is demonstrated: CD49A (Avg. 33% insulin+) and CD99 (Avg. 19% insulin+) as enrichment markers for insulin+ cells (positive selection markers) and CD66C and CD73 as enrichment markers for insulin− cells (negative selection markers).

The present invention, in some embodiments thereof, relates to insulin-producing cells derived from pluripotent stem cells, and methods of differentiating and purifying the same.

The prospect of producing islet-like clusters from human pluripotent stem cells is dependent on the possibility to obtain rather homogeneous populations of functional beta cells at the end of the differentiation process. According to some embodiments of the present invention, an antibody array was used in order to identify a set of antibodies that bind functional beta cells. The identified set of antibodies allow to purify cells having high expression of the Insulin, NKX6.1 and MAFA genes, from other insulin-expressing cells which are not yet functional. This purification step is critical to manufacture a homogeneous population, best suited for transplantation. The present invention is based in part on a systematic screening of combinations of antibodies and finding the best way to use them, for example by conducting immunostaining followed by magnetic bead cell sorting. The present invention also provides antibodies that remove non-relevant cells by using negative sorting.

An iterative high throughput screening which identifies and associates cell surface markers with a functional, cell-specific property such as insulin production is also provided. The technique, termed functional cell-capture screening (FCCS), is compatible with screening many surface markers for multiple functionalities in limited and heterogeneous samples. The efficiency and specificity of this approach is herein demonstrated by identifying novel markers enriching for pancreatic endocrine-type cells. This strategy may allow isolation of clinically relevant cells for treatment of diabetes.

Type I diabetes is caused by the autoimmune destruction of the insulin-producing beta cells. Insulin administration does not prevent the long-term complications of the disease, because of the cumulative damage of hyperglycemia periods on the vasculature. Replacement of the damaged cells with regulated insulin-producing cells is considered the ultimate cure for type 1 diabetes. Pancreas transplantation has been successful but is severely limited by the shortage of donors.

An alternative to forced expansion of post-mitotic β cells is the induction of differentiation of stem cells, (which have a natural self-expansion capacity), into insulin-producing cells. Various groups have suggested different differentiation protocols based on the typical differentiation pathways that operate during intra-uterine development (see for example D'Amour, Nature Biotechnology 2006; Jiang, Stem cells, 2007; and Kroon Nature Biotechnology 2008). However, to date, directed differentiation of embryonic stem cells has generated cells that only produce low amounts of insulin, compared to beta cells.

In an attempt to generate populations of cells that would be effective for treating Diabetes, the inventors of the present invention devised novel purification protocols and demonstrated that the purified cells synthesized high levels of insulin.

The phrase "pluripotent stem cells" as used herein, refers to cells which are capable of differentiating into the three embryonic germ cell layers, i.e., endoderm, ectoderm and mesoderm.

According to one embodiment, the pluripotent stem cells comprise embryonic stem cells and/or induced pluripotent stem cells.

The phrase "embryonic stem cells" refers to embryonic cells which are capable of differentiating into cells of all three embryonic germ layers (i.e., endoderm, ectoderm and mesoderm), or to remain in an undifferentiated state. Suitably, said embryonic cells or partially differentiated cell progenitors comprise human cells obtained only by methods that do not involve the destruction of embryos. Such methods were described, for example by Chung et al., Cell Stem Cell, 2008, 2(2), 113-117. It will be appreciated that commercially available stem cells can also be used with this aspect of the present invention. Human ES cells can be purchased from the NIH human embryonic stem cells registry. Non-limiting examples of commercially available embryonic stem cell lines are BG01, BG02, BG03, BG04, CY12, CY30, CY92, CY10, TE03 and TE32.

Induced pluripotent stem cells (iPS; embryonic-like stem cells), are cells obtained by induction of pluripotency in adult somatic cells (i.e., being capable of differentiating into the three embryonic germ cell layers, i.e., endoderm, ectoderm and mesoderm). According to some embodiments of the invention, such cells are obtained from differentiated tissues (e.g., a somatic tissue such as skin) and undergo induction of pluripotency by genetic manipulation which re-program the cell to acquire embryonic stem cells characteristics. According to some embodiments of the invention, the induced pluripotent stem cells are formed by inducing the expression of Oct-4, Sox2, Kfl4 and c-Myc in a somatic stem cell.

iPS cells can be generated from somatic cells by genetic manipulation of somatic cells, e.g., by retroviral transduction of somatic cells such as fibroblasts, hematopoietic stem cells, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); I H Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

It will be appreciated that undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernable cell junctions. Additional features of undifferentiated stem cells are further described herein under.

Currently practiced ES culturing methods are mainly based on the use of feeder cell layers which secrete factors needed for stem cell proliferation, while at the same time, inhibit their differentiation. Feeder cell free systems have also been used in ES cell culturing, such systems utilize matrices supplemented with either serum or serum replacement, cytokines and growth factors as a replacement for the feeder cell layer.

Feeder-Free Cultures

Stem cells can be grown on a solid surface such as an extracellular matrix (e.g., vitronectin or laminin) in the presence of a culture medium.

Following expansion of the pluripotent stem cells, the present invention contemplates culture thereof in a differentiation medium so as to differentiate the pluripotent stem cells into endoderm cells.

The present invention contemplates culturing the pluripotent stem cells under adherent conditions (attached to extracellular matrix coated plates) or under suspension (in non tissue culture-treated plates). Contemplated extracellular matrices include, but are not limited to MATRIGEL® (Becton Dickenson), laminin, fibronectin, proteoglycan, entactin, heparan sulfate, cultrex, Poly-lyzin and the like, alone or in various combinations.

An "adherent culture" refers to a culture in which cells in contact with a suitable growth medium are present, and can be viable or proliferate while adhered to a substrate. A "non-adherent culture" refers to a culture in which cells are typically in suspension with a suitable growth medium, and can be viable or proliferate while not being adhered to a substrate.

Methods of generating endoderm cells from pluripotent stem cells are known in the art and include for example use of Nodal (NM_018055; NP_060525.3) and small molecules (see for example Borowiak et al Cell Stem Cell, Volume 4, Issue 4, 348-358, 3 Apr. 2009). Alternatively, endoderm cells may be generated via embryoid bodies. Specifically, hES cells may be cultured in suspension without bFGF to generate embryoid bodies. The endodermal cells may be selected out of the EBs, see for example (Segev, Fischman, Ziskind et al., Stem cells, 2004; 22(3):265-74.

The phrase "pancreatic progenitor cells" refers to a population of cells which are not fully differentiated into pancreatic cells, yet are committed to differentiating towards at least one type of pancreatic cell—e.g. beta cells that produce insulin; alpha cells that produce glucagon; delta cells (or D cells) that produce somatostatin; and/or F cells (or gamma cells) that produce pancreatic polypeptide.

Typically, pancreatic progenitor cells express some of the phenotypic markers that are characteristic of pancreatic lineages (e.g. GLUT2, PDX-1 Hnf3β, PC1/3, Beta2, NKX2.2 and PC2). Typically, they do not produce progeny of other embryonic germ layers when cultured by themselves in vitro, unless dedifferentiated or reprogrammed. It will be appreciated that it is not implied that each of the cells within the population have the capacity of forming more than one type of progeny, although individual cells that are multipotent pancreatic progenitor cells may be present.

In certain embodiments, the terms "enriched", "isolated", "separated", "sorted", "purified" or equivalents thereof refer to a cell culture or a cell population or cell sample that contains at least about 50%, 55%, 60%, 65%, 70%, 75%, 80%, 85%, 90%, 95%, or 100% of the desired cell lineage or a desired cell having a certain cell phenotype, e.g., expressing a certain cell marker or not expressing a certain cell marker gene characteristic of that cell phenotype.

The terms "isolating" and "isolation" according to the present invention encompass not only selecting a pure population of a specific cell type but also selecting a cell population that is enriched in cells of a specific type.

Selecting according to the present invention refers to the process of distinguishing between the cells of interest and at least one other type of cells. The selecting process thus leads to enrichment of cells of interest.

Committed lineages of stem cells according to the present invention refer to the step in differentiation by which the initial pluripotent cell gradually becomes more committed towards the final cell fate of a functional insulin-producing cell. Initially, the pluripotent stem cells differentiate via mesendoderm into definitive endoderm. The definitive endoderm then commits towards a pancreatic cell fate, and these cells in turn differentiate towards an endocrine pancreatic cell fate, after which they commit to beta cells. According to some embodiments the hESCs are obtained by methods that do not involve the destruction of embryos.

As used herein, "marker", "epitope", "target", or equivalents thereof can refer to any molecule that can be observed or detected. For example, a marker can include, but is not limited to, a nucleic acid, such as a transcript of a specific gene, a polypeptide product of a gene, such as a membrane protein, a non-gene product polypeptide, a glycoprotein, a carbohydrate, a glycolipid, a lipid, a lipoprotein or a small molecule (for example, molecules having a molecular weight of less than 10,000 amu). A "cell surface marker" is a marker present on the cell surface.

The term "cell-surface marker relevant to the cells" denotes a marker which can be used for enrichment of a cell population from a heterogeneous population of cells, either by positive selection (selecting cells expressing said marker) or by negative selection (excluding cells expressing this marker).

As used herein, "ligand" refers to a moiety or binding partner that specifically binds or cross-reacts to the marker or target or receptor or membrane protein on the cell or to the soluble analyte in a sample or solution. The target on the cell, includes but is not limited to a marker. Examples of such ligands include, but are not limited to, an antibody that binds a cellular antigen, an antibody that binds a soluble antigen, an antigen that binds an antibody already bound to the cellular or soluble antigen; a lectin that binds to a soluble carbohydrate or to a carbohydrate moiety which is a part of a glycoprotein or glycolipid; or functional fragments of such antibodies and antigens that are capable of binding; a nucleic acid sequence sufficiently complementary to a target nucleic acid sequence of the cellular target or soluble analyte to bind the target or analyte sequence, a nucleic acid sequence sufficiently complementary to a ligand nucleic acid sequence already bound to the cellular marker or target or soluble analyte, or a chemical or proteinaceous compound, such as biotin or avidin. Ligands can be soluble or can be immobilized on the capture medium (i.e., synthetically covalently linked to a bead), as indicated by the assay format, e.g., antibody affinity chromatography. As defined herein, ligands include, but are not limited to, various agents that detect and react with one or more specific cellular markers or targets or soluble analytes. Examples of ligands are those described herein which selectively bind to a target and/or epitope including, but without limitation, CD49A, or any of the ligands and/or agents and/or antibodies which selectively bind to those targets. Further, all such ligands are characterized by the desired ability to bind the specified marker or target or analyte, whether it is soluble or bound to a cell. In one preferred embodiment, the ligand is a component that preferentially binds to all or a portion of a cell surface receptor. Thus, a ligand useful in this embodiment can be an antibody, or a fragment thereof, capable of binding to a cell surface receptor on a hES or hES-derived cells.

As used herein, the terms "contacting" or "exposing" or equivalents thereof refer to combining or mixing. For example, putative IgG, IgM, IgA, IgD, IgE or hybrids, derivatives or fragments of any of the aforementioned antibodies, can be contacted with a hES-derived cell population, including a population containing endoderm lineage cells. In some embodiments, formation of a complex between the hES-derived cell and the IgG, IgM, IgA, IgD IgE or hybrids, derivatives or fragments of any of the aforementioned antibody molecules refers to the ability of the target, receptor or membrane protein to selectively bind to the immunoglobulin molecule, or binding portion thereof, in order to form a stable complex that can be measured (i.e., detected) or quantified. Selective binding between a target, receptor or membrane protein and an immunoglobulin molecule, or binding fragment thereof, for example, is effected under conditions suitable to form a complex; such conditions (e.g., appropriate concentrations, buffers, temperatures, reaction times) as well as methods to optimize such conditions are known to those skilled in the art, and examples are disclosed herein. Examples of complex formation conditions are also disclosed in, for example, in Sambrook et al., Molecular Cloning: A Laboratory Manual, Cold Spring Harbor Labs Press, 1989, the reference Sambrook et al., ibid. is incorporated by reference herein in its entirety.

As used herein, the term "detecting complex formation" refers to determining if any complex is formed, i.e., assaying for the presence (i.e., existence) of a complex. If complexes are formed, the amount of complexes formed can, but need not be, determined. Complex formation, or selective binding, between the target, receptor and/or membrane protein and any immunoglobulin molecule in the composition can be measured (i.e., detected, determined) using a variety of methods standard in the art (see, for example, Sambrook et al. supra), examples of which are disclosed herein.

As used herein, the term, "antibody" refers to immunoglobulin molecules and immunologically active portions of immunoglobulin (Ig) molecules, i.e., molecules that contain an antigen binding site that specifically binds (immuno reacts with) an antigen. Such antibodies or fragments include polyclonal antibodies from any native source, and native or recombinant monoclonal antibodies of classes IgG, IgM, IgA, IgD, and IgE, hybrid derivatives, and fragments of antibodies including Fab, Fab' and F(ab')2, humanized or human antibodies, recombinant or synthetic constructs containing the complementarity determining regions of an antibody, an Fc antibody fragment thereof, a single chain Fv antibody fragment, a synthetic antibody or chimeric antibody construct which shares sufficient CDRs to retain functionally equivalent binding characteristics of an antibody that binds a desired cell surface receptor, and a binding fragment produced by phage display. Certain classes have subclasses as well, such as IgG1, IgG2, and others. Furthermore, in humans, the light chain can be a kappa chain or a lambda chain. Reference herein to antibodies includes a reference to all such classes, subclasses and types of human antibody species. Antibodies used in the examples described herein were generally obtained by conventional hybridoma methods and purified from ascites fluid by ammonium sulfate (45%) precipitation, centrifugation and affinity chromatography using protein A. The standard process of making monoclonal antibodies is described in G. Kohler and C. Milstein, 1975 Nature, 256: 495-497. Of course, the particular method of making and the type of monoclonal antibody is not limited to such techniques and it is envisioned that any technique for making such antibodies is within the practice of the embodiments described herein.

As used herein, a "solid matrix" or a "solid phase capture medium" refers to any matrix or medium which allows it to be separated from the cell population sample, for example, a physiologically compatible bead. Characteristics of such a matrix or medium include refractive index, size, light scatter intensity, or carrying a fluorescent detector dye to provide a unique fluorescent signature. Such beads are conventionally available in the art. For example, one subset of solid phase capture medium includes stable colloidal particles, such as polystyrene beads ranging in size from between about 0.2 to about 5.0 microns in diameter (i.e., colloidal-sized). Such polystyrene substrates or beads can contain aldehyde and/or sulfate functional groups, such as the commercially available beads, e.g., from Interfacial Dynamics Corporation, Portland, Oreg.

As used herein, "expression" refers to the production of a material or substance as well as the level or amount of production of a material or substance. The emerging hES-derived cell populations are assessed by phenotypic markers, and expression patterns are analyzed to determine not only which factors have a positive or negative influence on the differentiation pathway, but also particularly, which cell types they generate. Thus, determining the expression of a specific marker refers to detecting either the relative or absolute amount of the marker that is expressed or simply detecting the presence or absence of the marker. Stated another way, if a marker is a protein, polypeptide or fragment or portion thereof, there are various methods of measuring and quantifying protein expression for the presence and abundance (levels) of one or more proteins in a particular cell or tissue. One method is to perform a Western blot against the marker/protein of interest, whereby cellular lysate is separated on a polyacrylamide gel and then probed with an antibody to the protein of interest. The antibody can either be conjugated to a fluorophore or to horseradish peroxidase for imaging or quantification. Another commonly used method for assaying the amount of a particular protein in a cell is to fuse a copy of the protein to a reporter gene such as Green fluorescent protein (GFP), which can be directly imaged using a fluorescent microscope.

In some embodiments, the phrase "does not express" and equivalents thereof refer to non-detectable expression of a marker or substance. In other embodiments, the phrase "does not express" and equivalents thereof refer to marker expression that is detectable but insignificant. In certain embodiments, insignificant marker expression refers to a marker expression that is detectable by sensitive techniques, such as quantitative polymerase chain reaction, but which is not appreciably detectable by less sensitive techniques such as immunocytochemistry.

Typically, the selecting is effected using antibodies that are capable of specifically recognizing this cell-surface protein. Although the present invention contemplates additional agents such as polynucleotides or small molecules.

Antibody Array:

Antibody array screenings were performed using the procedure described in Sharvikin et al. ibid. Arrays were printed in a Microgrid printer with solid pins (Total array Systems, BioRobotics) on hydrogel coated slides (Full Moon Biosystems) using a panel of 231 monoclonal mouse anti-human antibodies (BD biosciences). Antibodies of human cell-surface markers were printed at a concentration of 0.5 mg/ml in five spots, each using a single stamp and with 750 .mu.m spacing. Following printing, the arrays were hydrated in a humidifier at 4.degree. C. for 48 hours, and then dried for 10 minutes at room temperature.

The FCCS Procedure:

Cells were dissociated using TrypLE™ Express (Invitrogen 12604) for 4 min, followed by quenching with 10% FBS in PBS. They were then seeded on the array at a total concentration of about $0.5*10^6$ cells/ml in 250-500.mu.l of human islets medium, supplemented with 2.mu.l of DNase (Ambion 2 U/.mu.l). Prior to incubation of cells on the array, the printed area was blocked for 3 minutes with 1% BSA in PBS solution. The blocking solution was replaced by the cell suspension, and the arrays were incubated for 1 hour at 37.degree. C. Excess cells were removed in a large volume of PBS and the arrays were fixed in 4% paraformaldehyde solution for 10 minutes. Cells on the array were permeabilized in 0.2% Triton™ X-100 solution for 20 min, washed twice with PBS and blocked for 45 min in blocking buffer (2% FBS, 2% BSA, 50 mM glycine in PBS). After blocking, arrays were washed twice with PBS and incubated for 2 hours at room temp in working buffer (1:10 diluted blocking buffer added 0.1% of Triton™) containing the primary antibodies: guinea-pig anti-insulin (DAKO, A0564), and rabbit anti-glucagon (DAKO, A0565) antibodies. Primary antibodies were removed and the arrays were washed three times with working buffer. Then, secondary antibodies were added in working buffer for a 45 min incubation period at room temp: cy5 donkey anti-guinea-pig (Jackson ImmunoResearch 706-175-148), AlexaFluor™ 488 donkey anti-rabbit (Jackson ImmunoResearch, 711-545-152), After the incubation period, arrays were washed three times in working buffer and imaged using automated, high content fluorescence microscopy (IXmicro, MDC).

Statistics: P-values of gene expression differences were computed using two-sample Paired t-test (one-tail) with equal variances. Number of repeats (n) represents biological replicates using samples derived from different batches.

Separation Methods:

Separation of the cells may be performed, in addition to, or in combination with the novel separation methods of the present invention, according to various physical properties, such as fluorescent properties or other optical properties, magnetic properties, density, electrical properties, etc. Cell types can be isolated by a variety of means including fluorescence activated cell sorting (FACS), protein-conjugated magnetic bead separation, morphologic criteria, specific gene expression patterns (using RT-PCR), or specific antibody staining.

The use of separation techniques include, but are not limited to, those based on differences in physical (density gradient centrifugation and counter-flow centrifugal elutriation), cell surface (lectin and antibody affinity), propidium iodide (PI) staining and vital staining properties (mitochondria-binding dye rho 123 and DNA-binding dye Hoechst 33342).

Various techniques can be employed to separate the cells. Monoclonal antibodies are particularly useful. The antibodies can be attached to a solid support to allow separation. The separation techniques employed should maximize the retention of viability of the fraction to be collected.

Various techniques of different efficacy may be employed to obtain "relatively crude" separations. Such separations are up to 30%, usually not more than about 5%, preferably not more than about 1%, of the total cells present are undesired cells that remain with the cell population to be retained. The particular technique employed will depend upon efficiency of separation, associated cytotoxicity, ease and speed of performance, and necessity for sophisticated equipment and/or technical skills. Procedures for separation may include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique.

Techniques providing accurate separation include fluorescence activated cell sorters, which can have varying degrees of sophistication, e.g., a plurality of color channels, low angle and obtuse light scattering detecting channels, impedance channels, etc. Other techniques for positive selection may be employed, which permit accurate separation, such as affinity columns, etc. Antibodies used for separation may be conjugated with markers, such as magnetic beads, which allow for direct separation, biotin, which can be removed with avidin or streptavidin bound to a support, fluorochromes, which can be used with a fluorescence activated cell sorter, or the like, to ease the separation of a particular cell type. Any technique may be employed which is not unduly detrimental to the viability of the remaining cells.

Enrichment of cells may be effected using known cell sorting procedures such as by a fluorescence-activated cell sorter (FACS).

As used herein, the term "flow cytometry" refers to an assay in which the proportion of a material (e.g. renal cells comprising a particular marker) in a sample is determined by labeling of the material (e.g., by binding a labeled antibody to the material), causing a fluid stream containing the material to pass through a beam of light, separating the light emitted from the sample into constituent wavelengths by a series of filters and mirrors, and detecting the light.

A multitude of flow cytometers are commercially available including for e.g. Becton Dickinson FACScan™ and FACScalibur™ (BD Biosciences, Mountain View, Calif.). Antibodies that may be used for FACS analysis are taught in Schlossman S, Boumell L, et al, [Leucocyte Typing V. New York: Oxford University Press; 1995] and are widely commercially available.

If the antibody is attached to a magnetic moiety (either directly, or indirectly through a cognate binding molecule), the heterogeneous cell population may be enriched for $CD49A^+$ cells by magnetic activated cell separation.

If the CD49A antibody is attached to an affinity moiety, the heterogeneous cell population may be enriched for $CD49A^+$ cells by affinity purification with the cognate binding molecule. Thus, for example, if the CD49A antibody is attached to biotin, the heterogenous cell population may be depleted of CD49A+ by purification with strepavidin beads or columns. The CD49A+ cells can subsequently be retrieved. If, for example the CD49A antibody is attached to an antibody or an Fc of an antibody, the heterogenous cell population may be depleted of CD49A+ by purification with protein A beads or columns. The CD49A+ cells can subsequently be retrieved.

It will be appreciated that since the differentiated cells of this aspect of the present invention typically grow as clusters, prior to cell sorting the heterogenous cell population should preferably be dispersed using a dispersing agent.

Examples of dispersing agents include, but are not limited to dispase, collagenase, accutase and trypsin. Alternatively, or additionally trituration may also be performed to increase the dispersion of the cells.

Following enrichment of CD49A+ cells, the cells are typically cultured for at least two more days, and preferably no more than 8 days (e.g. 2-6 days) under conditions that allow re-aggregation thereof. Typically, the cells are re-aggregated in the presence of an agent which inhibits calcium dependent cell-cell interactions. Examples of such agents include EDTA.

According to a particular embodiment, the re-aggregation is efficient at low glucose concentrations (i.e. lower than the glucose concentration of the initial differentiation stages). Exemplary ranges of glucose that are contemplated by the present inventors include 1-10 mM, more preferably 2-8 mM-e.g. 5.5 mM.

In order for re-aggregation to take place, the cells may be cultured in culture dishes (e.g. low-adherent binding plates) or may be seeded on a solid support (i.e. scaffold, as further described herein below).

Typical scaffolds contemplated by the present invention include those that are fabricated from collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol).

According to one embodiment, the scaffold is fabricated from a biocompatible polymer.

The phrase "biocompatible polymer" refers to any polymer (synthetic or natural) which when in contact with cells, tissues or body fluids of an organism does not induce adverse effects such as immunological reactions and/or rejections and the like. It will be appreciated that a biocompatible polymer can also be a biodegradable polymer.

The phrase "biodegradable polymer" refers to a synthetic or natural polymer which can be degraded (i.e., broken down) in the physiological environment such as by proteases. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients. Examples of biodegradable polymers include, but are not limited to, collagen (e.g., Collagen I or IV), fibrin, hyaluronic acid, polylactic acid (PLA), polyglycolic acid (PGA), polycaprolactone (PCL), poly(Lactide-co-Glycolide) (PLGA), polydioxanone (PDO), trimethylene carbonate (TMC), polyethyleneglycol (PEG), Collagen, PEG-DMA, Alginate, chitosan copolymers or mixtures thereof.

According to an exemplary embodiment, the scaffold comprises a porous alginate sponge.

Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, Ngn-3, NeuroD and Islet-1.

Markers characteristic of cells of the beta cell lineage are well known to those skilled in the art, and additional markers characteristic of the beta cell lineage continue to be identified. These markers can be used to confirm that the cells treated in accordance with the present invention have differentiated to acquire the properties characteristic of the beta-cell lineage. Beta cell lineage specific characteristics include the expression of one or more transcription factors such as, for example, Pdx1 (pancreatic and duodenal homeobox gene-1), NKX2.2, NKX6.1, Isl1, Pax6, Pax4, NeuroD, Hnf1b, Hnf-6, Hnf-3beta, and MafA, among others. These transcription factors are well established in the art for identification of endocrine cells. See, e.g., Edlund (Nature Reviews Genetics 3: 524-632 (2002)).

The efficiency of differentiation may be determined by exposing a treated cell population to an agent (such as an antibody) that specifically recognizes a protein marker expressed by cells that express markers characteristic to the pancreatic endocrine lineage. Alternatively, the efficiency of differentiation may be determined by exposing a treated cell population to an agent (such as an antibody) that specifically recognizes a protein marker expressed by cells that express markers characteristic of the beta cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Following differentiation and maturation the final product may be enriched for pancreatic islet cells, e.g. by using a computer-controlled robotic arm linked to a microscope in order to select and harvest the areas with islet morphology or alternatively by using FACS and selecting for a particular marker. This procedure avoids the risk of contamination with pluripotent ES cells and risks of teratoma after implantation of the cells in vivo.

Since the islet cells of the present invention express insulin, they may be used for treating a disease which is associated with insulin deficiency such as diabetes.

It will be appreciated that cells committed to the pancreatic endocrine lineage that do not yet express insulin levels similar to those in naturally occurring islets may also be used for implantation (immature islet cells), provided they co-express Pdx 1, NKX6.1 and MAF-A. These cells might be stimulated to maturate, i.e to express high levels of insulin, when they are in the correct in vivo environment.

Thus, according to another aspect of the present invention there is provided a method of treating diabetes in a subject, the method comprising transplantation of a therapeutically effective amount of the islet cells of the present invention into the subject, thereby treating diabetes.

As used herein "diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentrations, presence of glucose in the urine and excessive discharge of urine.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "transplanting" refers to providing the islet cells of the present invention, using any suitable route. Typically, beta cell therapy is effected by injection using a catheter into the portal vein of the liver, although other methods of administration are envisaged (e.g. subcutaneous or intraperitoneal or in fat tissues).

The islet cells of the present invention can be derived from an autologous sources, semi-autologous sources or from allogeneic sources. Since non-autologous cells are likely to induce an immune reaction when administered to the body several approaches have been developed to reduce the likelihood of rejection of non-autologous cells. These include either suppressing the recipient's immune system or encapsulating the non-autologous cells in immune-isolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylideneacetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore sizes as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

If appropriate, the patient can be further treated with pharmaceutical agents or bioactives that facilitate the survival and function of the transplanted cells. These agents may include, for example, insulin, members of the TGF-beta family, including Activin A, TGF-beta1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin-like growth factors (IGF-I, II) growth differentiation factor (GDF-5, -6, -7, -8, -10, -11, -15), vascular endothelial cell-derived growth factor (VEGF), Hepatocyte growth factor (HGF), pleiotrophin, endothelin, Epidermal growth factor (EGF), beta-cellulin, among others. Other pharmaceutical compounds can include, for example, nicotinamide, glucagon like peptide-I (GLP-1) and II, GLP-1 and 2 mimetibody, Exendin-4, retinoic acid, parathyroid hormone. Indolactam V, or PMA, or MAPK inhibitors, such as, for example, compounds disclosed in U.S. Published Application 2004/0209901 and U.S. Published Application 2004/0132729.

The cells of the present invention may be transplanted to a human subject per se, or in a pharmaceutical composition where it is mixed with suitable carriers or excipients.

As used herein a "pharmaceutical composition" refers to a preparation of one or more of the cell populations described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manners using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in context of the present invention include compositions wherein the active ingredients are contained in an amount effective to achieve the intended purpose. More specifically, a therapeutically effective amount means an amount of active ingredients (insulin producing cells) effective to prevent, alleviate or ameliorate symptoms of a disorder (e.g., Diabetes) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models (e.g. STZ diabetic mice) to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending on the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The present invention also contemplates incorporating the cells into a three-dimensional support. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissues, as well as to deliver chemotactic agents for inducing tissue growth, and are suitable for use in practicing the methods of the present invention. See, for example, the materials disclosed in U.S. Pat. Nos. 5,770,417, 6,022,743, 5,567,612, 5,759,830, 6,626,950, 6,534,084, 6,306,424, 6,365,149, 6,599,323, 6,656,488, U.S. Published Application 2004/0062753 A1, U.S. Pat. Nos. 4,557,264 and 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945.

The support may also be incorporated with at least one pharmaceutical compound that is an inhibitor of fibrosis, such as, for example, compounds disclosed in U.S. Pat. No. 6,331,298.

The support may also be incorporated with at least one pharmaceutical compound that is capable of enhancing angiogenesis, such as, for example, compounds disclosed in U.S. Published Application 2004/0220393 and U.S. Published Application 2004/0209901.

The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-beta family, including TGF-beta1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Prog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

A Procedure for Pluripotent Stem Cells Differentiation Into Insulin Producing Cells Pluripotent stem cells were grown in 2D, using E8 medium and vitronectin coating. Confluent cultures (80-90%) were harvested by EDTA (0.5 mM) dissociation. Following EDTA removal, single cell suspension was supplemented with Rock inhibitor (10 uM). Cells were seeded in dynamic suspension conditions (0.5-1×10$^6$ cells/ml) on either ultra-low binding 6 well plates, Erlenmeyer flasks or spinner flasks for the purpose of uniform aggregates formation (40-80 um) for 48 hours, with 80% media change one day following aggregation. Following 48 hours of aggregation, aggregates were subjected to a novel differentiation protocol.

The differentiation protocol utilizes three basic mediums; RPMI-1640™ DMEM-High Glucose and CMRL-1066™. On the first day of differentiation (day 0), the cells were washed with PBS and RPMI-1640™ media supplemented with CHIR (3 uM), Activin-A (100 ng/ml), FCS 0.2%, ITS 1:5000, Pen-strep and Glutamax™. On day 1, 80% media was changed to RPMI-1640™ media supplemented with Activin-A (100 ng/ml), FCS 0.2%, ITS 1:5000, Pen-strep and Glutamax™. On day 2, 80% media was changed to RPMI-1640 media supplemented with KGF (50 ng/ml), TGFb-RI (2.5 uM), FCS 0.2%, ITS 1:1000, Pen-strep and Glutamax™. On day 3, 80% media was changed as in day 2, without the TGFb-RI. On days 5 and 6, 80% media was changed to DMEM-High Glucose media supplemented with 1% B27, RA luM, KGF 50 ng/ml, SANT1 0.25 uM, TBP 200 nM, LDN 100 nM, Ascorbic-Acid 0.25 mM, Pen-strep and Glutamax™. On days 7, 9, 10 and 12, 80% media was changed to DMEM-High Glucose media supplemented with 1% B27, RA 0.1 uM, KGF 50 ng/ml, SANT1 0.25 uM, AA 0.25 mM, Pen-strep and Glutamax™. On days 13 and 15, 80% media was changed to DMEM-High Glucose media supplemented with 1% B27, RA 0.1 uM, SANT1 0.25 uM, EGF 10 ng/ml, ALK5i 10 uM, T3 luM, Heparin 10 ug/ml, GS1xx™ 1 uM, AA 0.25 mM, Pen-strep and Glutamax™. On days 17 and 19, 80% media was changed to DMEM-High Glucose media supplemented with 1% B27, EGF 10 ng/ml, ALK5i 10 uM, T3 luM, Heparin 10 ug/ml, GSIxx™ luM, AA 0.25 mM, Pen-strep and Glutamax. From day 20, 80% media was changed to CMRL-1066 media supplemented with 10% FCS, ALK5i 10 uM, T3 luM, N-Acetyl-Cysteine 0.5 mM, AXLi 1 uM, Pen-strep and Glutamax™, changed every other day.

Example 2

Use of Functional Cell-Capture Screen (FCCS) to Identify Cell Surface Markers that Enrich the Percentage of Insulin$^+$ Cells An iterative high throughput screen which identifies cell surface markers associated with cell type-specific functionality was used. The analysis was performed in three steps which can be iterated to refine the identification of markers for the desired cells. In the first step, a heterogeneous sample is dissociated into single cell suspensions and seeded on a glass slide printed with 231 different antibodies against cell-surface marker antigens (each antibody spot is represented in 5 replicates). Since the capture of cells on the array is based on recognition of antigens by the printed antibodies, the populated spots provide a list of cell surface markers expressed by the ensemble of cells in the heterogeneous sample. Each marker may be expressed by one or more cell types within the sample. To determine the association between the identified markers and a desired cell type, the cells on the array were immunostained with antibodies marking cell type-specific functionality. Analysis was performed by imaging the arrays with automated, high content fluorescence microscopy (ImageXpress Micro) and calculating the fraction of cells positive for the relevant functional label for each spot. Spots enriched with labeled cells define candidate surface markers for enrichment of cells with the desired functionality. The cells were sorted by FACS using these markers and validated the cell type-specific enrichment by measuring expression levels of relevant functional genes. To further refine the enrichment, the procedure was repeated with cells that were sorted using the validated markers.

As shown in FIG. 1, ES-derived pancreatic cells were analyzed by the functional cell capture screening. Following short incubation of single cells on the cell surface antibody array, cells were fixed and stained for insulin (green). Using high content screening analysis, the total number of bound cells to each spot was determined. In addition, the percentage of insulin$^+$ cells in each spot was calculated (Table 1). An example of output signal for four markers was demonstrated: CD49A (Avg. 33% insulin$^+$) and CD99 (Avg. 19% insulin$^+$) as enrichment markers for insulin$^+$ cells (positive selection markers). The percentage of insulin+ cells was the first step in defining the relevant population. Still, at the analysis stage, it was found that some markers represent insulin positive cells that were polyhormonal. These markers are considered negative selection markers also due to lack of NKX6.1 expression: CD26, CD49F, CD294 along with the very low insulin expressing cells CD73 and CD66C.

TABLE 1

The percentage of insulin+ cells using the specific cell-surface marker

| Cell-Surface marker | % of Insulin+ cells |
|---|---|
| CD29 | 47.9 |
| CD49A | 33 |
| CD10 | 32 |
| CD59 | 26 |
| CD294 | 24 |
| CD165 | 22 |
| CD99 | 19 |
| CD141 | 18 |
| CD26 | 8.65 |
| CD49f | 8.3 |
| G46-2.6 | 5.82 |
| CD44 | 2.84 |
| CD340 | 2 |
| CD66C | 1.3 |
| CD73 | 1 |

Example 3

Cell Sorting Using Cell Surface Antibodies

Figure 2:
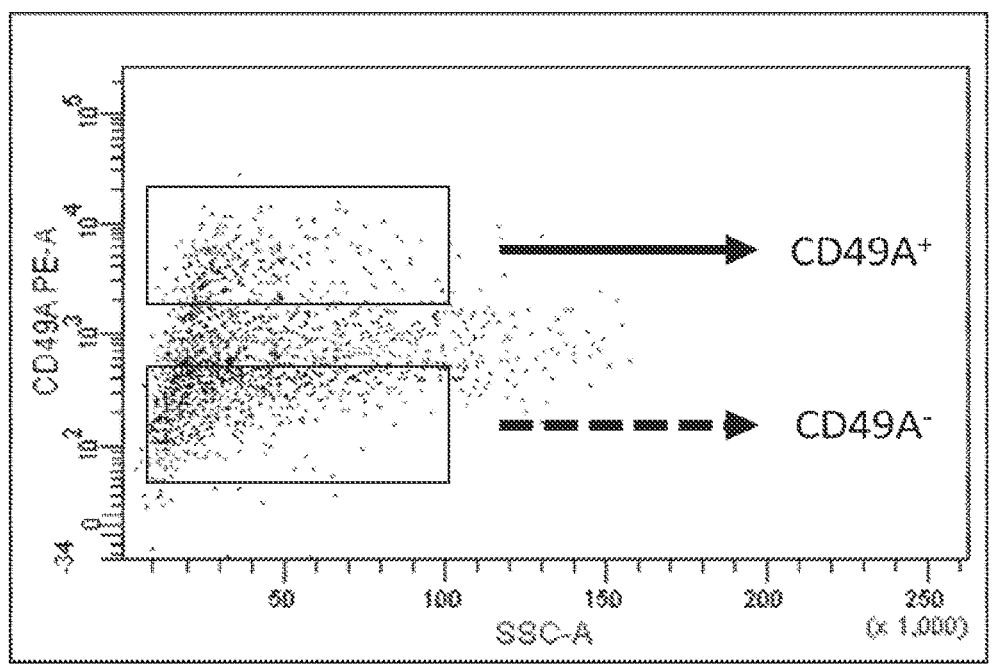
FIG. 2 demonstrates the functional sorting of positive selection markers. ES-derived pancreatic cells were dissociated and incubated with a PE-conjugated anti human CD49A antibody. Following the incubation, cells were washed 3 times and sorted for CD49A+ and CD49A− populations using FACS ARIA II.

Cell sorting was performed using a cell surface antibody, which came up in the array. Cell surface marker analyses were performed using the following fluorochrome-conjugated antibodies (BD biosciences Biolegend): CD10-FITC, CD49-PE, CD294-APC-Cy7, CD26-PE or CD26-PercPcy5.5, CD200-APC (no. 329207), CD73-PE-Cy7 (no. 344009), CD57-APC (no. 322313), CD59-FITC (no. 304706), CD340—PercPcy5.5 (no. 324415) and CD49F-PE-CY7 (no. 313622). Cell aggregates were washed in PBS and then enzymatically dissociated to single-cell suspensions using TryplE™ (Invitrogen) at 37° c. Then, cells were put in FACS buffer (PBS with 0.5% BSA and 1% FBS).Cells were incubated with surface markers for 30 min in 4° c. Cells were then washed in PBS and centrifuged for 5 min at 350 g. Cell sorting was conducted using Flow cytometry, suspended cells were filtered through a 40.micron nylon strainer (BD Falcon), and analyzed/sorted by FACSAria™ flow cytometer (BD). Thresholds were determined using unstained samples or single stained samples. Gates were taken in the far edges of each population to avoid intersection As shown in FIG. 2, ES-derived pancreatic cells were dissociated and incubated with a PE-conjugated anti human CD49A antibody (BioLegend, 328304). Following incubation, cells were washed three times and sorted for CD49A+ and CD49− populations using FACS ARIA II™ (BD).

Example 4

Validation by Real-Time Quantitative PCR

RNA from sorted populations of cells was isolated using RNeasy micro kit (Qiagen 74004). DNA was eliminated using RNAse-free DNase kit (Qiagen 79254) and the mRNA was converted to cDNA using high-capacity cDNA Reverse Transcription kit (Applied Biosystems 4368814). Transcript levels were measured using real-time qPCR on a Step-one-plus Real-Time PCR System using Taqman Fast advanced master mix (Applied Biosystems 4444557). The levels of each gene was normalized using HPRT, GAPDH or TBP as an endogenous control mRNA. The catalog numbers of the primers used for the qPCR are listed in Table 2:

TABLE 2

The primers used for the qPCR

| | ABI | IDT |
|---|---|---|
| NKX6.1 | | Hs.PT.58.25073618 |
| HPRT | HS99999909_M1 | |
| Glucagon | | Hs.PT.58.14706508 |
| AFP | Hs00173490_m1 | |
| Rfx6 | Hs00543100_m1 | |
| Ngn3 | | Hs.PT.53a.19734677g |
| Sox9 | | Hs.PT.58.38984663 |
| Cdx2 | Hs01078080_m1 | |
| TBP | Hs00427621_m1 | |
| MAFA | | HS.PT.58.14570025.g |
| Insulin | Hs02741908_m1 | |

Figure 3:
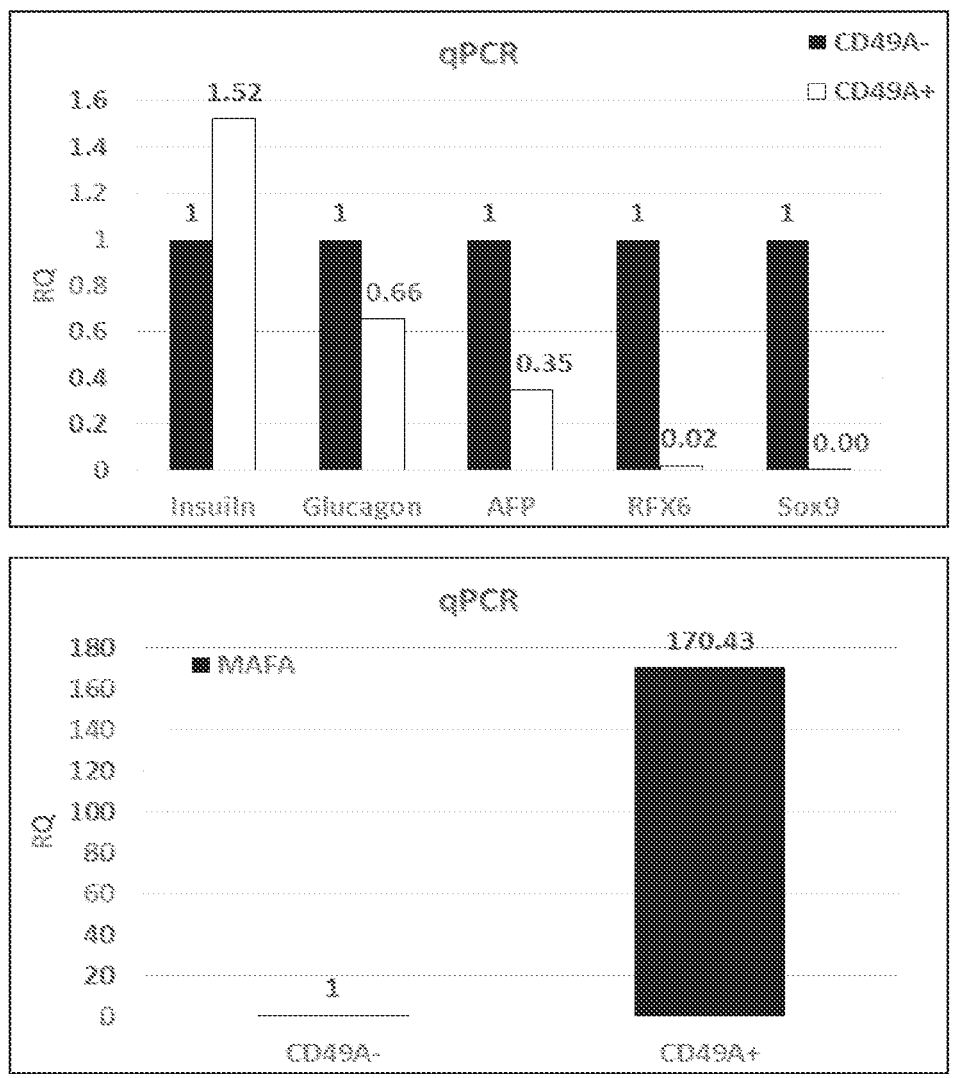
FIG. 3 shows a molecular analysis of CD49A sorted populations. RNA was purified from sorted ES-derived pancreatic cells populations. QPCR analysis demonstrated 52% higher expression of insulin mRNA in the CD49A+ population relative to the CDA49− population. Furthermore, the CD49A+ population demonstrated 34% reduction in glucagon expression, supporting the notion that CD49A enrichment is mainly to insulin producing cells and not to glucagon producing cells. The expression of early pancreatic developmental markers like RFX6 and Sox9 is markedly decreased in the CD49A+ population, suggesting that these cells have a mature phenotype. The most notable change in the highly expressed genes is in MAFA expression; that is ×170 higher in the CD49A+ population compared to the CD49A− population. Gene expression is normalized to TBP/HPRT mRNA using the 2-ΔΔ Ct method, relative expression to CD49A− population (RQ=1).
Figure 4A:
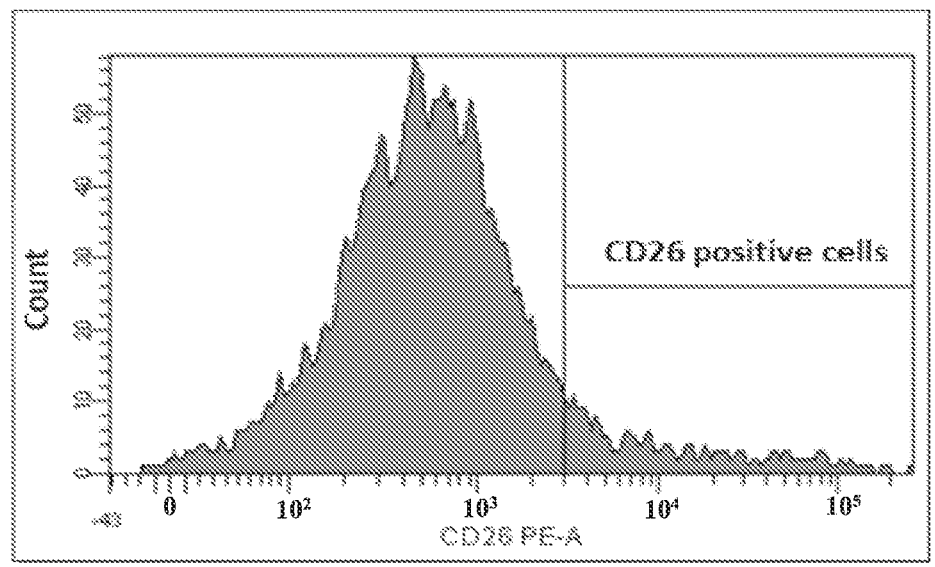
FIGS. 4A-D show the functional sorting of negative selection markers. ES-derived pancreatic cells were dissociated and incubated with a PE-conjugated anti human CD26 (A) or anti human CD73 antibodies (B). Cells sorted for CD26− (C) or CD26+ (D) were internal stained for GCG. Following incubation, cells were washed three times and sorted for CD+ and CD− populations using FACS ARIA II.
Figure 4B:
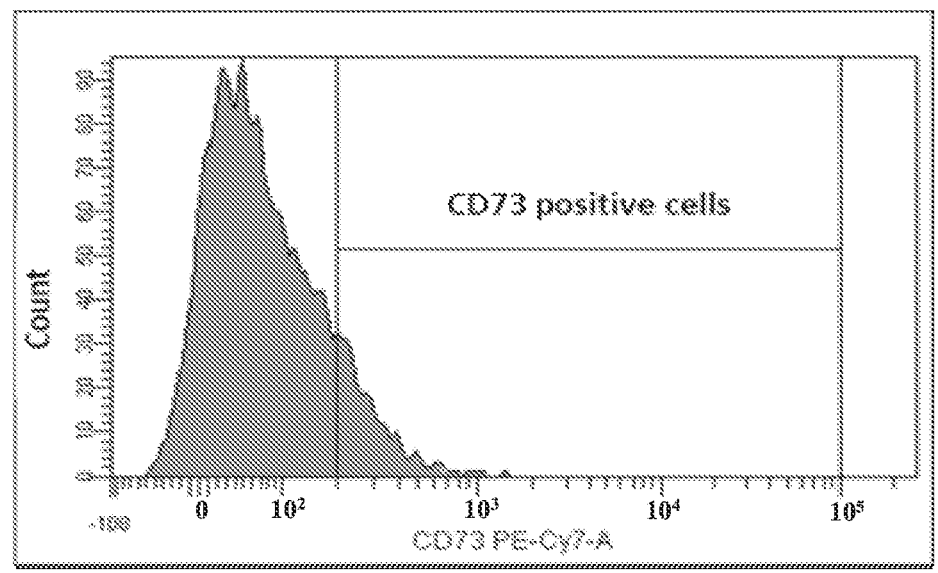
Figure 4C:
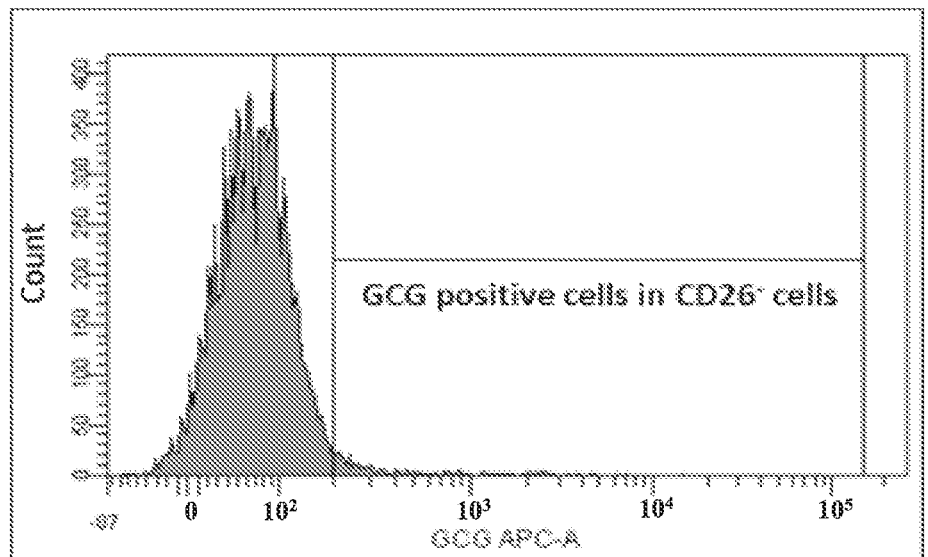
Figure 4D:
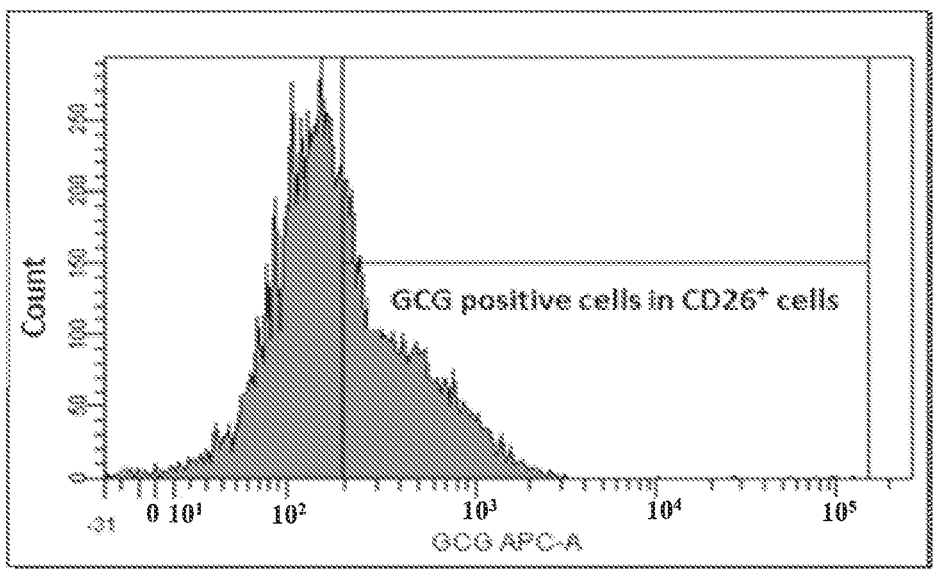

As shown in FIG. 3, RNA was purified from CD49A+ sorted ES-derived pancreatic cells populations. QPCR analysis demonstrated 52% higher expression of insulin mRNA in the CD49A+ population relative to the CDA49− population. Furthermore, the CD49A+ population demonstrated 34% reduction in glucagon expression, supporting the fact that CD49A enriches mainly insulin producing cells and not glucagon producing cells. The expression of early pancreatic developmental markers like RFX6 and Sox9 is markedly decreased in the CD49A+ population, suggesting that these cells have a mature phenotype. The most notable change in the highly expressed genes is in MAFA expression; in the CD49A+ population MAFA is expressed over ~×170 fold higher than in the CD49A− population. Gene expression is normalized to TBP/HPRT mRNA using the 2-ΔΔ Ct method, relative expression to CD49A− population (RQ=1).

Example 5

Functional Sorting of Negative Selection Markers

The functional sorting of negative selection markers is demonstrated in FIGS. 4A-D. ES-derived pancreatic cells were dissociated and incubated with a PE-conjugated anti human CD26 (A) or anti human CD73 antibodies (B). Cells sorted for CD26− (C) or CD26+ (D) were internal stained for GCG. Following incubation, cells were washed three times and sorted for CD+ and CD− populations using FACS ARIA II (BD).

Figure 5:
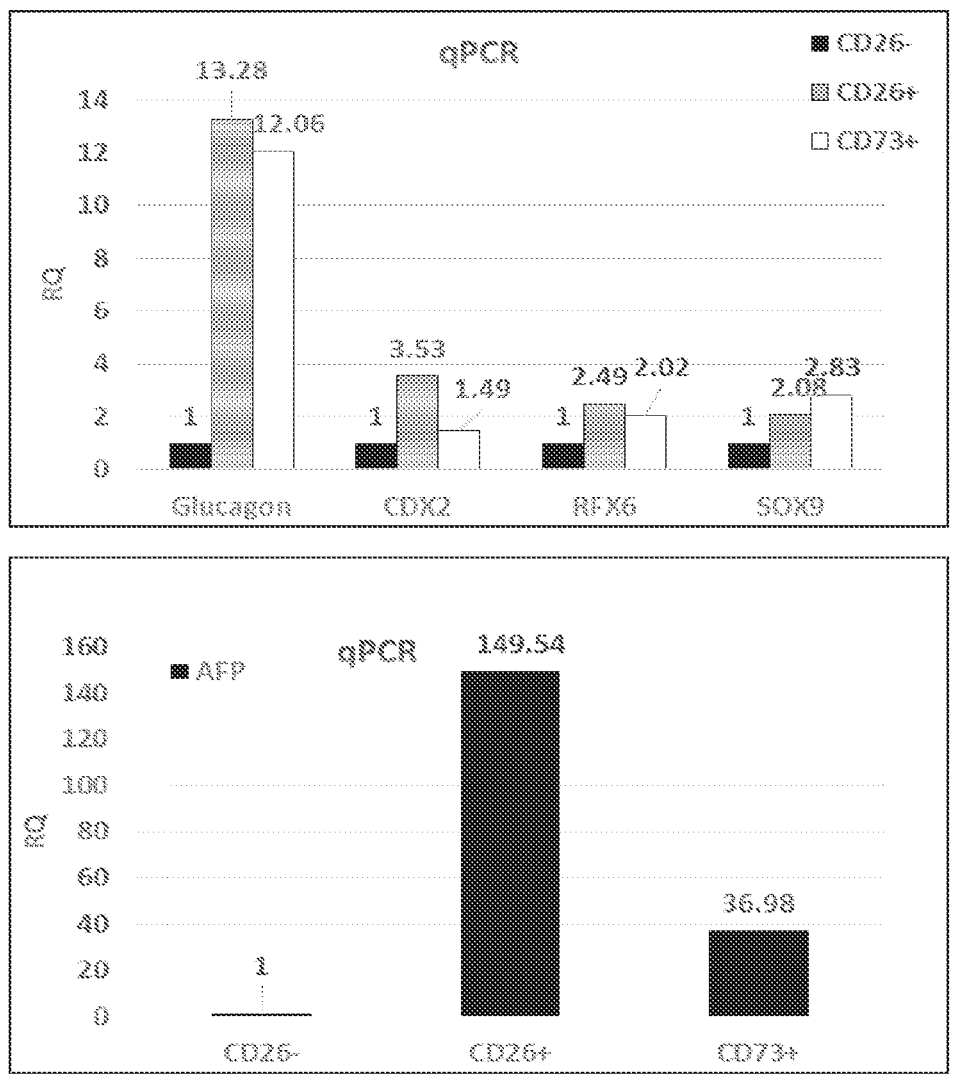
FIG. 5 shows the molecular analysis of CD26/CD73 sorted populations. RNA was purified from sorted ES-derived pancreatic cells populations. QPCR analysis demonstrated that both CD26+ and CD73+ populations demonstrated higher expression of glucagon mRNA relative to the negative population. Furthermore, the positive populations demonstrated higher expression of early pancreatic developmental markers like RFX6 and Sox9, suggesting that the CD26− population have a more mature phenotype. The most notable change in the highly expressed genes is in AFP, a non-pancreatic, hepatic lineage marker. AFP is highly expressed in the CD26+ population and to a lesser extent in the CD73+ population. Gene expression is normalized to TBP/HPRT mRNA using the 2-ΔΔ Ct method, relative expression to CD26− population (RQ=1).

As shown in FIG. 5, RNA was purified from sorted ES-derived pancreatic cells populations. QPCR analysis demonstrated that both CD26+ and CD73+ populations demonstrated higher expression of glucagon mRNA relative to the negative population. Furthermore, the positive populations demonstrated higher expression of early pancreatic developmental markers such as RFX6 and Sox9, suggesting that the CD26− population have a more mature phenotype. The most notable change in the highly expressed genes is in AFP, a non-pancreatic lineage marker. AFP is highly expressed in the CD26+ population and to a minor extent in the CD73+ population. Gene expression is normalized to TBP/HPRT mRNA using the 2-ΔΔ Ct method, relative expression to CD26− population (RQ=1).

Example 6

Assessment of the Secretion Capacity of the Sorted Cell Population In Vivo

The selected cell population was isolated by MACS. Antibodies for the specific cell surface markers were attached to magnetic beads. Cells were flushed through the beads and attached based on the expression of their cell surface markers. The isolated pure populations were taken to GSIS studies in vitro. Populations that double the amount of secreted insulin in response to high glucose (20 mM) compared to low glucose (3.3 mM) were considered positive.

The cell populations that show high expression of NKX6.1/Insulin, low expression of Glucagon or non-beta cell markers and are GSIS positive were transplanted under the kidney-capsule of SCID mice to assess their secretion capacity in vivo.

For the in vivo experimental procedures, immuno-deficient mice of the SCID/Beige strain (7-8 weeks) were used.

A control group of ten untreated mice was compared to a group of ten implanted mice. Following an acclimatization period of 5 days, the mice were weighed. On the first day of the experiment, an analgesic was administered subcutaneously, at least half an hour before the surgical procedure, followed by general anesthesia with 2-3% Isoflurane inhalation.

Implantation Under the Renal Capsule:

Skin was cut diagonally at the left lateral region of the body, behind the rib cage, followed by incision of the abdominal wall.

Kidney implantation under the capsule was performed in the left kidney that was pulled gently out through the abdominal and skin incisions, rinsed with sterile saline, its capsule was punctured, and a hollow-fiber or catheter (about 1 cm long and 0.6 mm in diameter) was inserted, through which the ILCs were injected under the capsule. Kidney was returned to its anatomic location in the abdominal cavity. Number of cells that were implanted/injected per treated mouse: approx. $5\times10^6$. Abdominal wall was stitched with Vicryl 5-0 sutures and the skin was closed with wound clips. Analgesics was injected for pain relief for at least 48 hours after the surgical procedure.

Figure 6:
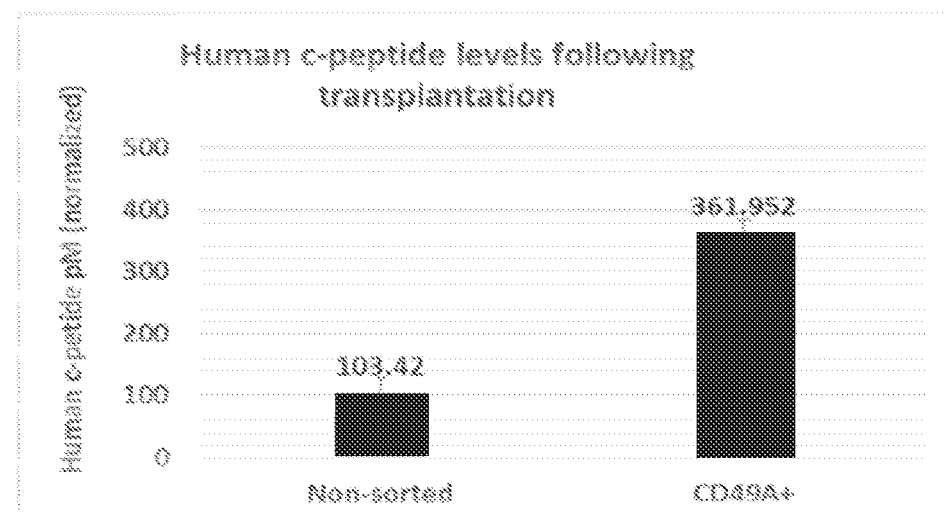
FIG. 6 demonstrates the results of the transplantation of MACS purified CD49A+ expressing cells under the kidney capsule of scid-beige mice. HESC derived pancreatic cells at the final stages of differentiation, were sorted based on their CD49A expression. Sorted and non-sorted cells were transplanted into mice. Approximately 2-3 weeks following transplantation hPSCs-derived CD49A+ transplanted cells (3~4×10^6 cells/mouse) demonstrated 3 fold higher in vivo function compared to non-sorted cells.

As shown in FIG. 6, three fold higher in vivo function were measured in mice transplanted with hPSCs-derived CD49A+ cells ($3\sim4\times10^\wedge6$ cells/mouse) compared to mice transplanted with non-sorted cells.

Implantation of a Subcutaneous Transplant Device:

Skin will be cut at top left region of the body, above the rib cage, parallel to the spine. A subcutaneous pocket will be created and the device will be inserted in it, under the skin. Incision will be closed with wound clips. Number of cells implanted per device in treatment groups: approx. $5\times10^6$. Analgesics will be injected for pain relief for at least 48 hours after the surgical procedure.

Animals will be followed for 10-12 weeks by: clinical follow-ups on a daily basis; checking their body weight on a weekly basis; and checking their c-peptide (human) blood levels every 2 weeks (using species specific ELISA kits), this will allow the evaluation of cell function, (e.g., their ability to secrete insulin). Test procedure: mice will be deprived of food for 12 hours before the test. They will then be injected with 50% dextrose at a dose of 2 mg per gram of body weight. 45 minutes after that injection, blood samples will be collected for assessing the level of C-peptide, under light anesthesia, from the retro-orbital sinus. Overall blood volume collected shall not exceed 10% of the overall blood volume of each mouse.

Upon termination of the experiment, animals will be euthanized by inhalation of $CO_2$. The implanted kidney or device will be removed (post-mortem) and preserved in Formalin solution for further analysis.

Example 7

An Alternative Procedure for Pluripotent Stem Cells Differentiation into Insulin Producing Cells
Growth of Pluripotent Stem Cells Before Differentiation Pluripotent stem cells were grown in 2D, using E8 medium and vitronectin coating. Confluent cultures (80-90%) were harvested by EDTA (0.5 mM) dissociation. Following EDTA removal by centrifugation, single cell suspension in growth medium E8 was supplemented with Rock inhibitor (10 uM). Cells were seeded in dynamic suspension conditions (0.5-1×106 cells/ml) on either ultra-low binding 6 well plates, Erlenmeyer flasks or spinner flasks for the purpose of formation of uniform aggregates or cell clusters (40-80 um) for 48 hours, with 80% media change one day following seeding. Following 48 hours of aggregation, aggregates were subjected to the defined differentiation protocol. During the differentiation protocol, medium change involved removing 80% of the old medium and adding back the same volume of fresh medium or new composition.

The ES cells expressed >95% stage-specific embryonic antigen 4 (SSEA4); TRA1-60>95% and 100% EpCam. C—X—C chemokine receptor type 4 (CXCR4) was expressed less than 0.2%. It was extremely important to start with pure pluripotent cells. No clustering and differentiation in suspension was obtained if less pluripotent cells were used.

STEP 1 Definitive endoderm 3 days

On day 0, the cells were washed with PBS and seeded in Medium A: MCDB 131 media supplemented with CHIR (3 uM), Activin-A (100 ng/ml), 0.25 mM Ascorbic acid, 2.46 g/l NaHCO3, Fatty acid-free bovine serum albumine (FAF-BSA) 0.5%, ITS 1:50,000, Glucose 8 mM, Pen-strep and Glutamax.

On day 1, 80% of the volume of the medium was changed to Medium B: MCDB 131 media supplemented with Activin-A (100 ng/ml), 0.25 mM Ascorbic acid, FAF BSA 0.5%, ITS 1:50000, 8 mM Glucose, Pen-strep and Glutamax.

STEP 2 Primitive gut tube—2 days

At day 2 of differentiation more than 95% of cells expressed CXCR4, SOX17>95% and FOXA2>95%.

On day 3, 80% of the volume of the medium was changed to Medium C: MCDB 131 media supplemented with KGF (50 ng/ml), 0.25 mM Ascorbic acid, 1.754 g/l NaHCO3, FAF BSA 0.5%, ITS 1:50000, 8 mM Glucose, Pen-strep and Glutamax.

On day 5, 80% of the volume of the medium was renewed as in day 3.

STEP 3 posterior foregut—2 days

On day 6, medium was changed to Medium D: MCDB 131 supplemented with 1.754 g/l NaHCO3, FAF BSA 2%, ITS 1:200, 8 mM Glucose, RA 1 uM, KGF 50 ng/ml, SANT1 0.25 uM, TBP 200 nM, LDN 100 nM, Ascorbic-Acid 0.25 mM, Pen-strep and Glutamax.

On day 7, medium was changed to Medium E: MCDB 131 media supplemented with 1.23 g/l NaHCO3, FAF BSA 2%, ITS 1:200, 8 mM Glucose, RA 1 uM, KGF 50 ng/ml, SANT1 0.25 uM, TBP 200 nM, LDN 100 nM, Ascorbic-Acid 0.25 mM, Pen-strep and Glutamax.

STEP 4 Pancreatic progenitors—4 days

On day 8 medium was changed to Medium F: MCDB 131 media supplemented with 1.23 g/l NaHCO3, FAF BSA 2%, ITS 1:200, 8 mM Glucose, RA 0.1 uM, KGF 50 ng/ml, SANT1 0.25 uM, TBP 100 nM, LDN 200 nM, Ascorbic-Acid 0.25 mM, Pen-strep and Glutamax.

At day 8 of differentiation more than 90-95% of cells expressed PDX1 and 1-2% expressed NKX6.1.

On day 10 new Medium F was added.

STEP 5 Pancreatic endocrine progenitors—3 days

On day 12 media was changed to Medium G:MCDB 131 supplemented with 1.754 g/l NaHCO3, FAF BSA 2%, ITS 1:200, 20 mM Glucose, ALK5i 10 uM, RA 0.05 uM, SANT1 0.25 uM, LDN 100 nM, T3 1 uM, Heparin 10 ug/ml, ZnSO4 10 uM. Ascorbic-Acid 0.25 mM, Pen-strep and Glutamax, At day 12 of differentiation more than 90-95% of cells expressed PDX1 and 60-70% of cells co-expressed PDX1 and NKX6.1.

On day 14 new Medium G was added.

STEP 6 Formation of beta cell-like population (PDX1+/NKX6.1+/insulin+)—8 days

On day 15, media was changed to Medium H: MCDB 131 media supplemented with 1.754 g/l NaHCO3, FAF BSA 2%, ITS 1:200, 20 mM Glucose, ALK5i 10 uM, LDN 100 nM, T3 1 uM, Heparin 10 ug/ml, ZnSO4 10 uM, GSiXX 0.1 uM, Ascorbic-Acid 0.25 mM.

At day 15 of differentiation 60% of cells expressed NKX6.1 and 5-15% expressed C-peptide. 3-5% of cells co-expressed NKX6.1 and C-peptide.

On days 17, 19 and 21 Medium H was renewed

STEP 7 Maturation of beta cell-like cells (PDX1+/NKX6.1+/Ins+/MAFA+)

On day 23, Medium was changed to Medium I: MCDB 131 media supplemented with 1.754 g/l NaHCO3, FAF BSA 2%, ITS 1:200, 20 mM Glucose, ALK5i 10 uM, T3 1 uM, Heparin 10 ug/ml, ZnSO4 10 uM, Trolox 10 uM, Ascorbic-Acid 0.25 mM, N-Acetyl-Cysteine 1 mM, AXLi 2 uM, Pen-strep and Glutamax, On day 24 Medium I was renewed.

On days 26, 28 and 30 Medium I was renewed before implantation. At day 20-30 of differentiation 40-60% of the cells expressed NKX6.1 and 40-48% expressed C-peptide. 15-30% of cells co-expressed NKX6.1 and C-peptide (Table 3).

The percentage of cells expressing the markers of differentiation CXCR4, PDX1, NKX6.1, and C-peptide was determined by flow cytometry using FACS Calibur (Becton Dickinson apparatus), using antibodies the following antibodies (all in a dilution of 1:100).

CXCR4; Biolegend, 306505
C-peptide; DSHB, GN-ID4
PDX1; BD, 563436
NKX6.1, BD, 563338

The measurements were conducted prior to the medium change at the end of each stage.

Figure 9:
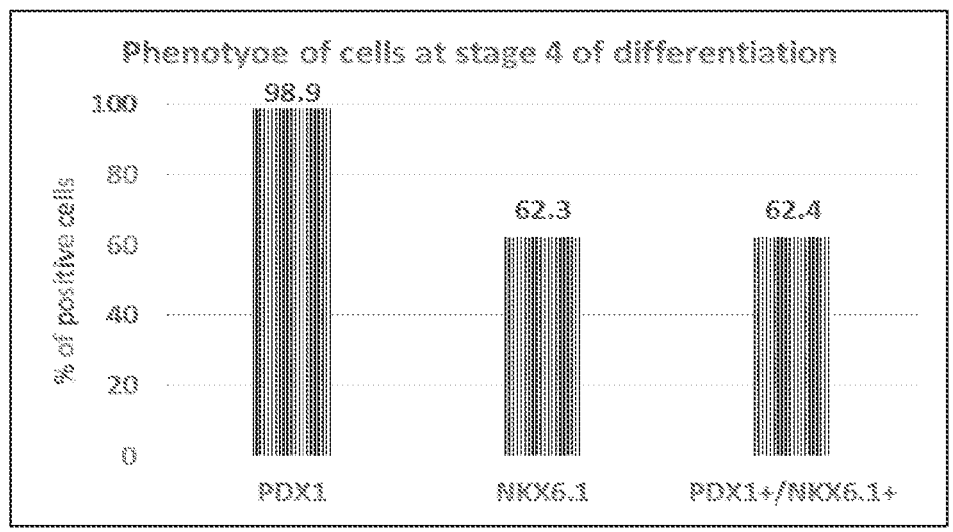
FIG. 9 represents typical distribution of the cell populations differentiated according to the protocol described in Example 7, as analyzed by FACS analysis. As demonstrated, the distribution of pancreatic progenitors (NKX6.1 and PDX1 double positive cells (62.3%)), while PDX1 positive cells represent respectively 98.9% and NKX6.1 62.4% of total cells.
Figure 10:
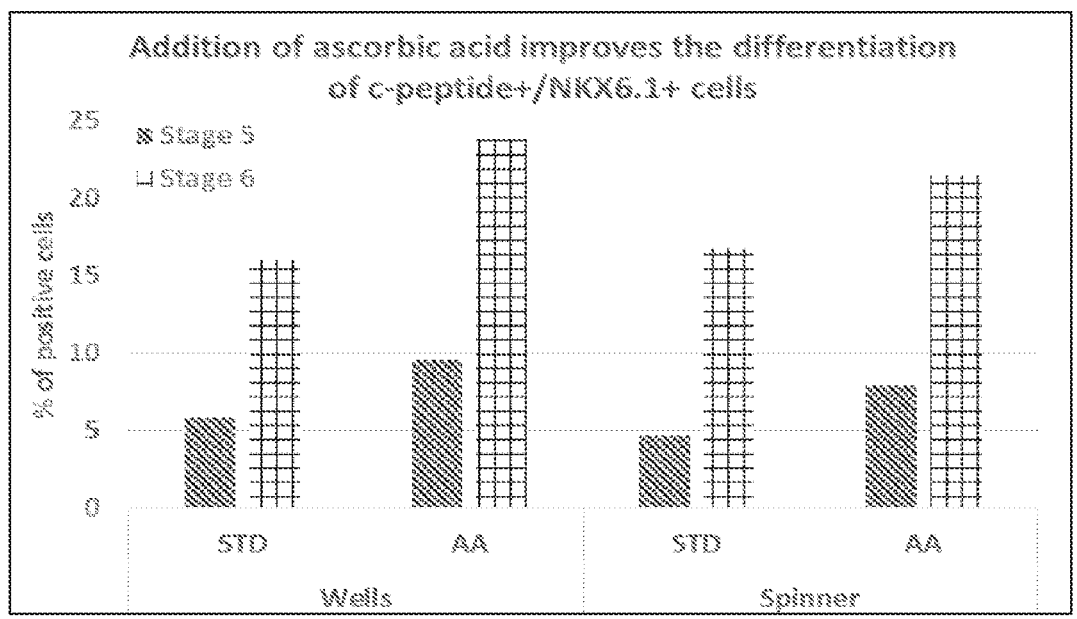
FIG. 10 shows a graphical representation of the percentage of NKX6.1/C-peptide double positive cells (Beta-like cells) in function of time of differentiation and treatment conducted either in wells or spinner flasks, emphasizing the effect of time and addition of ascorbic acid on the yield.
Figure 11:
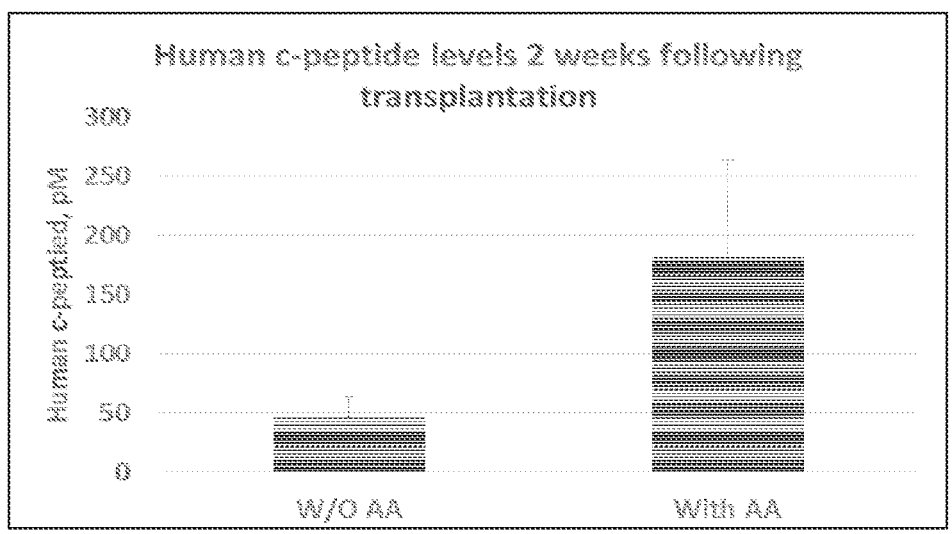
FIG. 11 shows the average of human c-peptide in mice blood following 2 weeks from transplantation. The advantage of adding ascorbic acid all over the differentiation protocol can be observed.

The kinetics of formation of NKX6.1/C-peptide double positive cells and the effect of addition of ascorbic acid from the beginning to the end of the differentiation protocol are shown in FIGS. 9-11.

The pluripotent stem cells were seeded in suspension and distributed into wells of 6 well plates (FIGS. 9-11), or seeded also into spinner flasks (FIG. 10) and markers of differentiation measured after the end of stage 4 (day 12), 5 (day 15), 6 (Day 20) and 7 (day 30). Regular media (Standard) contains ascorbic acid from day 0 to 8. The "treatment" consisted in addition of ascorbic acid from day 0 through all the stages of the differentiation (AA). The advantage of adding ascorbic acid all over the differentiation can be observed in FIGS. 10-11. The percentage of Beta-like cells is similar when cells are cultured in suspension in wells and in spinners. However, spinners request less manipulations, and the cell number recovered is usually higher than in wells.

TABLE 3

Phenotype of the cells at the end of different stages of the differentiation protocol

|  | Day 2 | Day 8 | Day 12 | Day 15 | Day 20 | Day 30 |
| --- | --- | --- | --- | --- | --- | --- |
| End of stage | 1 | 3 | 4 | 5 | 6 | 7 |
| CXCR4 | 99% |  |  | 5% |  |  |
| PDX 1 NKX6.1 DP |  | 1% | 80% | 70% | 60% | 40-60% |
| NKX6.1 C-peptide DP |  |  |  | 4-8% | 20-30% | 15-30% |

$5 \times 10^{\wedge}6$ cells differentiated according to the protocol described above, were implanted under the kidney capsule of immuno-deficient mice. 2 weeks following transplantation, animals were subjected to overnight fasting and then injected (IP) with 50% glucose solution (2 g/Kg). Blood was collected 30 minutes following glucose injection. The level of human C-peptide in the serum was measured by ELISA.

As demonstrated in FIG. 11, human insulin C-peptide was higher in the Ascorbic Acid (AA) treatment relative to the treatment without AA condition. In addition, these cells demonstrated structural organization as naïve human islets (FIG. 12).

Figure 12:
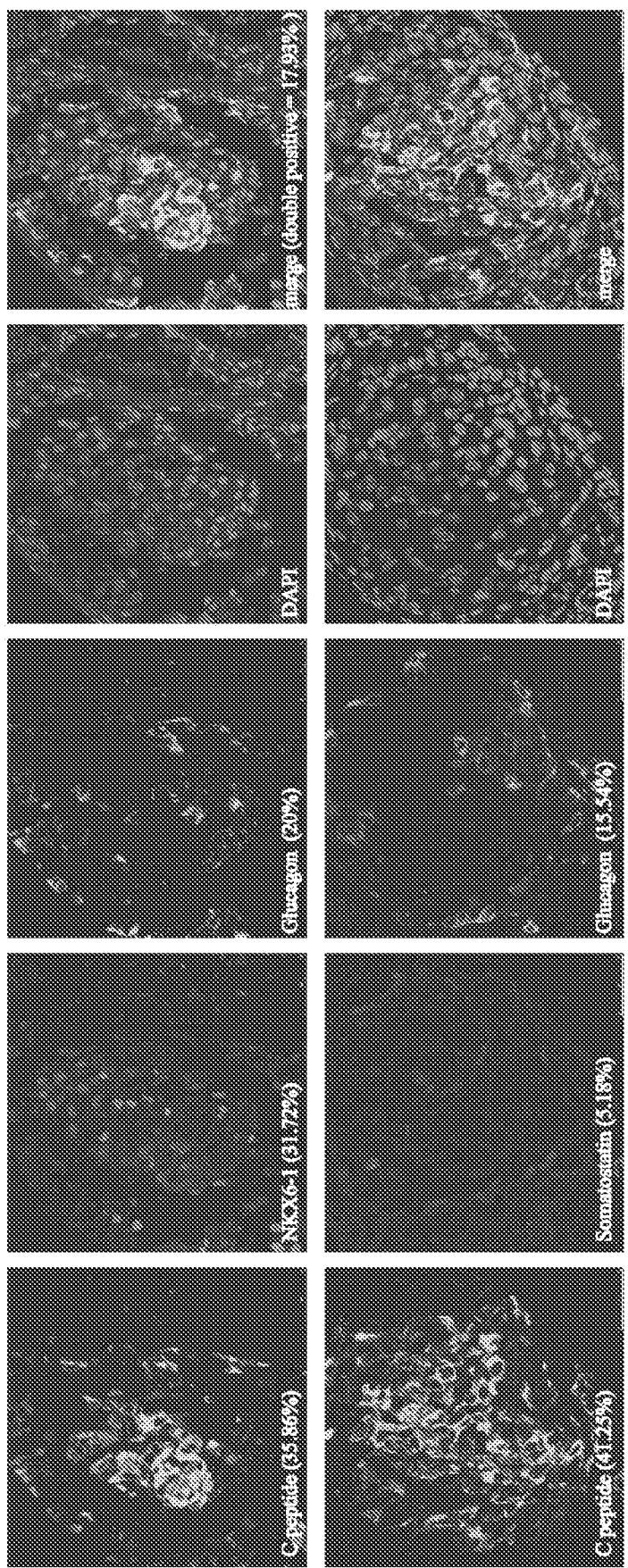
FIG. 12 shows the islet like clusters internal organization of transplanted cells following 2 weeks of transplantation. As demonstrated, the c-peptide+/NKX6.1+ are detected and are Glucagon negative. Somatostatin is expressed in very few cells.

As demonstrated in FIG. 12, the C-peptide+/NKX6.1+ were detected and were found to be Glucagon negative. Somatostatin was expressed in very few cells.

Example 8

Functional Sorting of Both Negative and Positive Selection Markers

Figure 7:
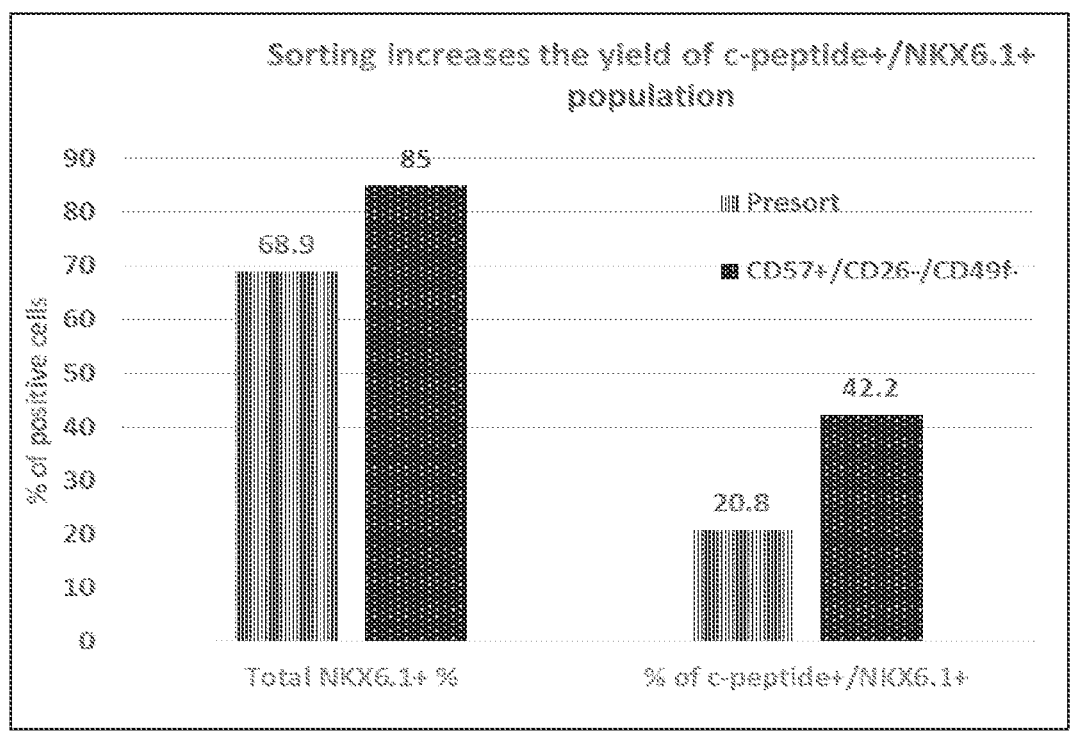
FIG. 7 demonstrates that the CD57+ CD26− CD49F− population yields 42.2% of c-peptide NKX6.1 double positive cells compared to 20.8% in the presorted population (A). The total NKX6.1+ cells is also increased from 68.9% in the presorted population to 85% in the CD57+ CD26− CD49F− population.
Figure 8A:
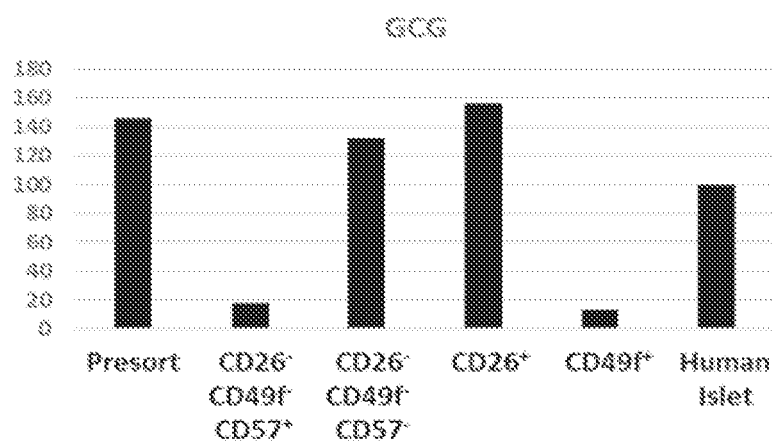
FIGS. 8A-D show the results of Real-time PCR of the sorted populations for glucagon (GCG) (A), glucagon-like-peptide-1 receptor (GLP-1R) (B), neurogenin 3 (NGN3) (C), and MAFA (D).
Figure 8B:
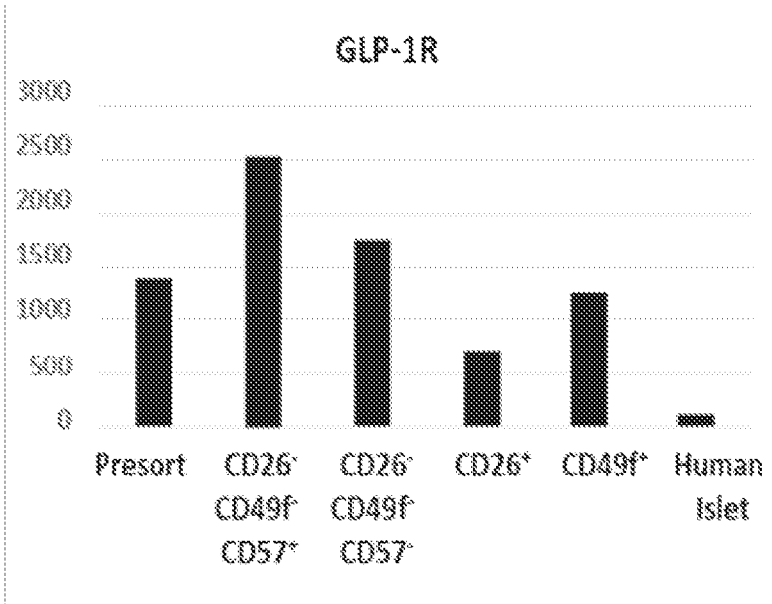
Figure 8C:
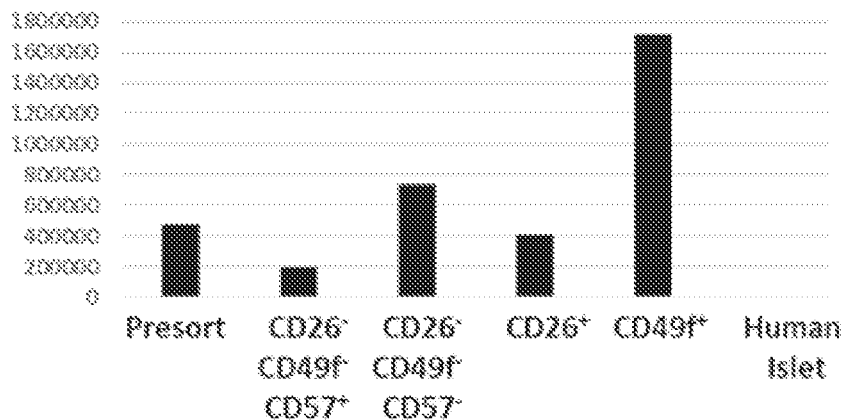
Figure 8D:
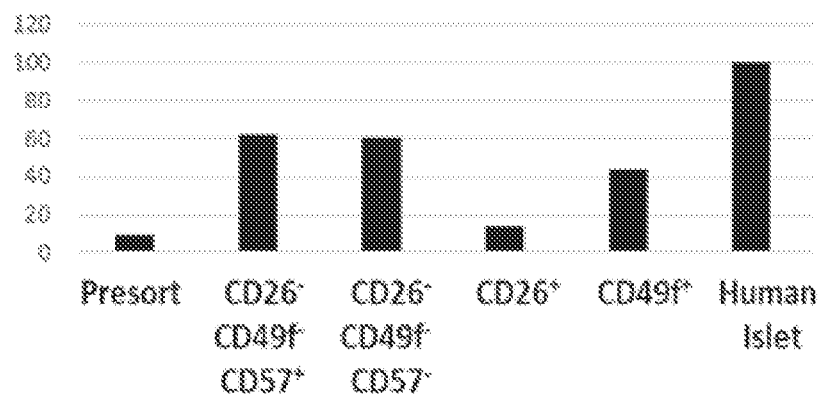

Cells in day 21 of differentiation grown as described in Example 7, were externally stained for CD49F, CD57 and CD26. Five populations were sorted according to their external markers. The sorted populations were internally stained for C-peptide and NKX6.1. As shown in FIG. 7, the CD57+ CD26− CD49F− population yields 42.2% of c-peptide NKX6.1 double positive cells (FIG. 7) compared to 20.8% in the presorted population. In addition, an increase in the total NKX6.1 percentage is also detected, implying true enrichment of the c-peptide+/NKX6.1+ cells. As shown in FIGS. 8A-D, the sorted populations were taken for RNA extraction and Real-time PCR was conducted for glucagon (GCG) (A), glucagon-like-peptide-1 receptor (GLP-1R) (B), neurogenin 3 (NGN3) (C), and MAFA (D).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of enriching for pancreatic endocrine cells expressing NKX6.1 and insulin comprising:
    a) exposing an in vitro cell population comprising pancreatic endocrine cells expressing NKX6.1 and insulin having been ex-vivo differentiated from pluripotent stem cells to a ligand that binds CD49a;
    b) exposing the in vitro cell population comprising pancreatic endocrine cells expressing NKX6.1 and insulin having been ex-vivo differentiated from pluripotent stem cells to a ligand that binds CD26;
    c) selecting cells which bind said ligand that binds CD49a and do not bind said ligand that binds CD26; and subsequently
    d) culturing said cells which bind said ligand that binds CD49a and do not bind said ligand that binds CD26, thereby enriching for pancreatic endocrine cells expressing NKX6.1 and insulin.

2. The method of claim 1, wherein the ligand that binds CD49a is an antibody or binding fragment thereof.

3. The method of claim 2, wherein said antibody is a monoclonal antibody.

4. The method of claim 1, wherein the ligand that binds CD49a is associated with a magnetic particle.

5. The method of claim 1, wherein the selecting is by fluorescence-based cell sorting or magnetic-field based cell sorting.

6. The method of claim 1, further comprising ex vivo differentiating pancreatic endocrine cells from human pluripotent stem cells prior to step (a).

* * * * *